US009095579B2

(12) United States Patent
Bier et al.

(10) Patent No.: US 9,095,579 B2
(45) Date of Patent: Aug. 4, 2015

(54) PROTECTION AND TREATMENT AGAINST INFLUENZA INFECTION

(71) Applicants: The Regents of the University of California, Oakland, CA (US); The Scripps Research Institute, La Jolla, CA (US)

(72) Inventors: Ethan Bier, San Diego, CA (US); Margery Smelkinson, San Diego, CA (US); Robert Krug, Austin, TX (US); Meghana Malur, Austin, TX (US); Michael Oldstone, La Jolla, CA (US); John Teijaro, La Jolla, CA (US)

(73) Assignees: THE REGENTS OF THE UNIVERSITY OF CALIFORNIA, Oakland, CA (US); THE SCRIPPS RESEARCH INSTITUTE, La Jolla, CA (US)

( * ) Notice: Subject to any disclaimer, the term of this patent is extended or adjusted under 35 U.S.C. 154(b) by 51 days.

(21) Appl. No.: 13/761,922

(22) Filed: Feb. 7, 2013

(65) Prior Publication Data

US 2013/0203793 A1 Aug. 8, 2013

Related U.S. Application Data

(60) Provisional application No. 61/595,756, filed on Feb. 7, 2012.

(51) Int. Cl.

| | |
|---|---|
| ***A61K 31/10*** | (2006.01) |
| ***A61K 31/435*** | (2006.01) |
| ***A61K 31/44*** | (2006.01) |
| ***A61K 31/4402*** | (2006.01) |
| ***A61K 31/438*** | (2006.01) |
| ***A61K 45/00*** | (2006.01) |
| ***A61K 45/06*** | (2006.01) |

(52) U.S. Cl.

CPC ............... *A61K 31/438* (2013.01); *A61K 31/10* (2013.01); *A61K 31/435* (2013.01); *A61K 31/44* (2013.01); *A61K 31/4402* (2013.01); *A61K 45/00* (2013.01); *A61K 45/06* (2013.01)

(58) Field of Classification Search

CPC ..... A61K 31/10; A61K 31/435; A61K 31/44; A61K 31/4402

USPC .......................................................... 514/278

See application file for complete search history.

(56) References Cited

U.S. PATENT DOCUMENTS

2004/0126359 A1 * 7/2004 Lamb et al. .................. 424/85.2

* cited by examiner

*Primary Examiner* — Yong Chong

(74) *Attorney, Agent, or Firm* — Sutherland Asbill & Brennan LLP

(57) ABSTRACT

Method and composition for protection and treatment against influenza viral infection by modulating the activity of at least one essential host signaling pathways, including the Hedgehog (Hh), the Bone Morphogenetic Protein (BMP), the Notch (N) signaling pathways or combinations thereof, which activity is altered by the viral protein NS1. The method and composition comprise use of a compound that modulates at least one of these essential host signaling pathways for preventing or controlling symptoms associated with influenza viral infection. The method or composition can also be used either alone or in combination with other therapeutic agents for treating or protecting against influenza infection, and associated syndromes.

2 Claims, 10 Drawing Sheets

PROTECTION AND TREATMENT AGAINST INFLUENZA INFECTION

CROSS REFERENCES TO RELATED APPLICATIONS

This application claims priority from U.S. Provisional Application Ser. No. 61/595,756 filed on Feb. 7, 2012, which is incorporated herein by reference in its entirety.

STATEMENT REGARDING FEDERALLY SPONSORED RESEARCH

This invention was made in part with Government support under Grant Nos. R01 AI070654, R01 AI11772, and 1F32 AI078672-01A1 awarded by the National Institutes of Health. The Government has certain rights in the invention.

FIELD OF THE INVENTION

This invention relates to influenza viral infection, and methods of prevention and treatment.

BACKGROUND OF THE INVENTION

Influenza has been the cause of yearly epidemics and global pandemics throughout history. The influenza virus has only eleven (11) genes, in which the multifunctional Non-Structural-1 protein (NS1) is one of 11 proteins encoded by influenza A virus (Lamb 2001; Hale et al. 2008) and is known to be indispensable for virulence. NS1 interacts with several viral and host components to subvert cellular defense mechanisms and promote viral replication via two domains: an N-terminal RNA-binding domain (RBD) and an effector domain (ED), both of which can multimerize (Hale et al. 2008). The RBD binds dsRNA, a common viral replication intermediate, thereby preventing dsRNA-dependent activation of multiple host viral defense pathways (Talon et al. 2000). The ED sequesters multiple host proteins required for cellular mRNA maturation and export and factors controlling apoptosis (Hale et al. 2008). These functions of NS1 benefit the virus by inactivating translation of new antiviral components, recruiting host translation machinery so that they can be utilized preferentially for viral mRNA translation, and extending host cell viability to ensure sufficient viral maturation can occur.

Most interactions between the influenza NS1 protein and its host targets have been identified in isolated cells grown in culture for which the assays are typically cell autonomous (e.g., viral replication, altered host gene expression). Novel targets of NS1 that might be involved in cell-cell communication were identified using *Drosophila melanogaster*, a well-developed genetic system for analyzing conserved signaling pathways (Reiter et al. 2001; Bier 2005) and for elucidating interactions between host and pathogen encoded proteins (Bier and Guichard 2012; Hughes et al. 2012). Due to the high degree of sequence conservation between disease genes in humans and flies, *Drosophila* can serve as a powerful yet inexpensive multicellular host model to study how influenza proteins interact with cellular components to manipulate the host. In contrast, most studies of viral factors have relied primarily on cell culture studies which are not well suited for identifying cell-cell interactions.

The Hedgehog (Hh) (Jiang and Hui 2008) and Notch (N) (Fortini 2009; Kopan and Ilagan 2009) signaling pathways play central roles in growth and development (Dufraine et al. 2008; Klusza and Deng 2011), tissue repair (Crosby and Waters 2010), and adult immune responses (Crompton et al. 2007; Ito et al. 2012) of vertebrates and invertebrates. In the *Drosophila* wing primordium (or wing disc), Hh is secreted from cells in the posterior compartment and binds to the Patched (Ptc) receptor, resulting in phosphorylation and surface accumulation of the seven pass transmembrane domain protein Smoothened (Smo) in a stripe of cells in the anterior compartment (referred to as the central organizer) (Hooper and Scott 2005). Activated Smo in turn recruits Costal-2 (Cos-2) to the plasma membrane, disrupting an inhibitory complex with the transcription factor Cubitus interruptus (Ci; Gli in mammals), thereby stabilizing and activating the full length Ci-155 protein (Wilson and Chuang 2010). In the absence of Hh signaling, microtubule associated Cos-2 promotes Ci-155 phosphorylation via cAMP-dependent Protein Kinase A (PKA) and other kinases, resulting in partial proteolysis of Ci-155 to a N-terminal repressor (Ci-75) that silences a subset of Hh target genes (Hooper and Scott 2005).

Notch signaling is required for a variety of binary cell fate decisions in many developmental contexts including specification of the dorsal-ventral compartment border in the *Drosophila* wing primordium (Irvine and Vogt 1997). When activated by the Delta or Serrate ligands, the Notch receptor undergoes a series of cleavage events leading to the generation of a free intracellular domain (N-ICD) (Fortini 2009; Kopan and Ilagan 2009). N-ICD forms a complex with the Suppressor of Hairless (Su(H)) protein, enters the nucleus, and acts a transcriptional cofactor to regulate Notch target gene expression.

There are very few effective drugs to treat influenza infection and these drugs (e.g., TAMIFLU) act on highly mutable extracellular proteins that function in the late phase of viral escape from the cell. Also, viral surface proteins which are the main targets for vaccines mutate rapidly to evade suppression. The fact that NS1 is involved in the pathogenicity of influenza A viruses makes it a good target to attenuate these viruses. Several studies demonstrated that influenza viruses with partial deletions in NS1 proteins are attenuated and do not cause disease, but induce a protective immune response in different species including mice (Hai et al. 2008; Talon et al., 2000), pigs (Solorzano et al, 2005; Vincent et al. 2007), horses (Quinlivan et al., 2005), birds (Steel et al., 2009) and macaques (Baskin et al., 2007). Although it had been known for more than a decade that influenza viruses with partial deletions in NS1 proteins were attenuated, all but one (Garcia-Sastre et al. 1998) NS1 truncation variants of influenza A viruses were generated by mutagenesis. Wang et al. (2008) later demonstrated that the naturally truncated variant (Garcia-Sastre et al. 1998) had propensity to generate new variants when passaged in ovo (Wang et al., 2008). The new variants were excellent live-attenuated influenza vaccine candidates (Wang et al., 2008). The ability to attenuate influenza viruses by truncation of the NS1 protein presents a great approach in design and development of the next generation live-attenuated influenza vaccines for both poultry and humans.

A significant source of mortality associated with influenza, particularly for highly virulent strains is an overly active host immune response often referred to as a cytokine storm. Cytokine storms lead to toxic-shock like symptoms and can be fatal. Agents that block cytokine storms associated with influenza or other diseases (e.g., acute allergies) could be a significant therapeutic value. Since many of the patients who secumb to highly virulent forms of influenza are young and otherwise healthy individuals, this target population may benefit most from therapies aimed at suppressing cytokine storms.

Knowledge of new host signaling responses to viral infection can lead to therapies targeted to these interactions. These treatments can be effective at suppressing the pathogenesis of many different strains of flu unlike vaccines which typically target only a few strains and require constant reformulation since the virus can evade host antibodies. There is a need to develop a new therapeutic approach for preventing and/or treating influenza through inhibiting influenza infection.

SUMMARY OF THE INVENTION

The invention provides a method for inhibiting influenza viral infection comprising administering to a subject in need an effective amount of a composition comprising a pharmaceutically acceptable carrier and a compound that modulates at least one host protein that interacts with NS1 viral protein, thereby altering at least one essential host signaling pathway selected from a Hedgehog (Hh) signaling pathway, a Bone Morphogenetic Protein (BMP) signaling pathway, and a Notch (N) signaling pathway, and combinations thereof. The invention provides a novel intracellular target that is known to play an essential role in virulence of seasonal as well and highly virulent forms of influenza. More specifically, the invention identifies a novel activity of the NS1 protein involved in regulating the essential host signaling pathways, e.g., Hh, BMP, or N signaling pathways, and combinations thereof, and thus, provides an effective approach for preventing and treating influenza viral infections.

In certain embodiments, the compound modulates the Hedgehog (Hh) signaling pathway, and the compound is an antagonist or inhibitor of the Hedgehog (Hh) signaling pathway. In certain embodiments, such Hh antagonist is cyclopamine or vismodegib. In other embodiments, due to variances of influenza viral strains, the significant differences in NS1 activities and associations with these essential signaling pathways in different host species, such as invertebrates vs. vertebrates, the compounds encompassed in the invention can also be an effective agonist or stimulator of the Hh signaling pathway.

In other embodiments, the compound modulates the Bone Morphogenetic Protein (BMP) signaling pathway, and the compound is an antagonist of the BMP signaling pathway. In other embodiments, due to variances of influenza viral strains, the significant differences in NS1 activities and its associations with these essential signaling pathways in difference host species, such as invertebrates vs. vertebrates, the compounds encompassed in the invention can also be an effective agonist or stimulator of the BMP signaling pathway.

In yet other embodiments, the compound modulates the Notch (N) signaling pathway, said compounds including an extracellular modulator influencing binding or activation of Notch by its ligands, inhibitors of Notch activation by membrane proteases such as gamma-secreates (e.g. DBZ), a cytoplasmic modulator influencing signal transduction steps after receptor activation, or a nuclear modulator influencing a transcriptional activity of Notch-CSL protein complex.

In certain embodiments, the composition of the invention can be used either alone or in combination with one or more other therapeutic agents, such as TAMIFLU, known for preventing or reducing severity of influenza viral infection, and associated syndromes thereof. The composition of the invention can be supplied as pills, inhalers, or sealed sterile vials to be parenterally administered or added to intravenous solutions to preventatively treat patients that are likely to have been exposed to influenza infection, or as a treatment to reduce the severity of infection for patients who are suspected or known to be infected by the virus.

A method is also provided for inhibiting influenza viral infection comprising modulating at least one host protein that interacts with NS1 viral protein, thereby altering at least one essential host signaling pathway, including, but not limited to, a Hedgehog (Hh) signaling pathway, a Bone Morphogenetic Protein (BMP) signaling pathway, or a Notch (N) signaling pathway, and thereby inhibiting influenza viral infection. In certain embodiments, the modulating step comprises administering an infection inhibiting amount of a compound that interferes a Hedgehog (Hh) signaling pathway, a Bone Morphogenetic Protein (BMP) signaling pathway, or a Notch (N) signaling pathway.

The invention also provides methods of screening for such effective candidate compounds that are inhibitors of influenza infections as well as methods for the manufacture of a medicament for the same beneficial inhibitory activity. Methods for screening for an effective candidate compound are well known in the art. An exemplary screening method includes administering candidate compounds to *Drosphila larvae* from strains expressing an NS1 transgene and screening for individuals with reduced wing phenotypes deriving from the effects of NS1. Another exemplary screening method includes expressing NS1 in *Drosophila* cell lines (e.g. S2 cells) carrying fluorescent Hh or N reporter constructs (e.g., GFP or luciferase) and then screening for compounds that reduce the effect of NS1 in such cells.

These and other inventions and variations will be apparent to one of skilled in the art in view of the present disclosure.

DETAILED DESCRIPTION OF THE INVENTION

Figure 1:
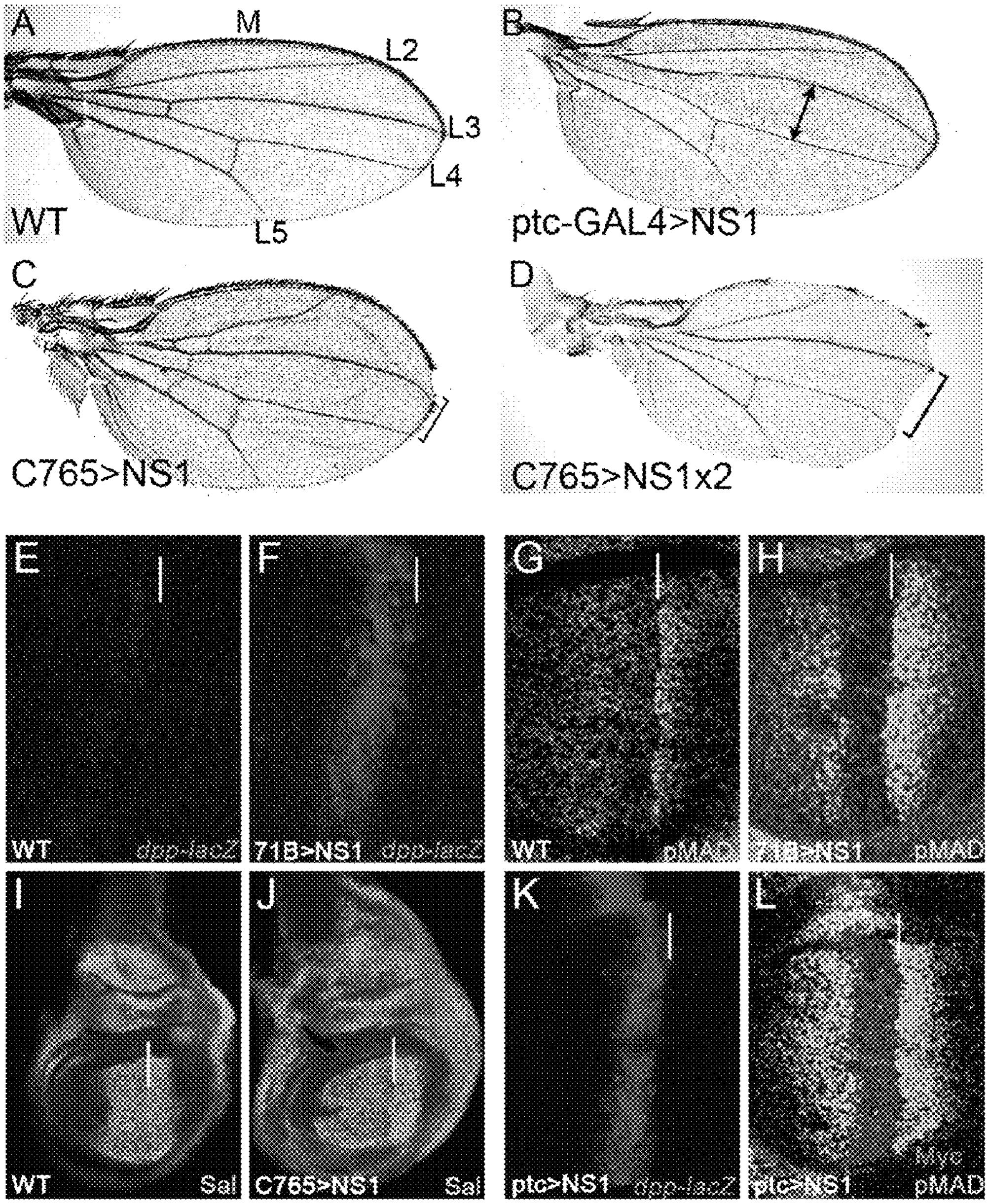
FIG. 1: NS1 enhances dpp expression and Dpp signaling in the fly. (A) A wild type wing with longitudinal veins labeled L2-L5, M=margin. (B, C) The distance between the L3 and L4 veins increases in wings expressing NS1 along the A/P border with the ptc-GAL4 driver (B, double arrow) or the ubiquitous C765-GAL4 driver (C), which is further exaggerated by two copies of NS1 (D) (brackets in C and D). In C and D, notches are also present along the margin (arrows). Wild type discs (E,G,I) or wing discs expressing NS1 under the control of the ubiquitous 71B-GAL4 (F, H), C765-GAL4 (J), or ptc-GAL4 (K,L) drivers stained with antibodies to visualize dpp-lacZ expression (E,F,K), phospho-Smad1(G,H,L), Spalt (I, J), or the Myc epitope tag (L). Ubiquitous expression of NS1 leads to elevated expression of dpp-lacZ (F vs. E), stronger and broadened pMAD expression (H vs.G), and expanded expression of the Dpp target gene Spalt (J vs. I). Restricted expression of NS1 along the A/P border (detected by the C-terminal Myc tag) also results in enhanced dpplacZ expression (K, vs. E) and pMAD staining in cells neighboring the A/P border (L vs. G). In all figures of wing discs, dorsal is up, anterior is to the left. White lines indicate the A/P border.

The invention provides compositions and methods for inhibiting influenza viral infection, including protection and treatment against influenza viral infection, by modulating the activity of at least one host protein that interacts with NS1 and thereby alters the activity of host signaling pathways, including, but not limited to, the Hedgehog (Hh), the Bone Morphogenetic Protein (BMP), and the Notch (N) signaling pathways. The invention provides a new role of NS1 viral protein in modifying cell-cell signaling via the Hh, BMP, and/or N pathways.

The invention thus provides a method and composition for inhibiting influenza viral infection, including protection against and treatment of influenza viral infection, comprising administering to a subject in need an effective amount of a composition comprising a pharmaceutically acceptable carrier and a compound that modulates NS1 viral protein associated essential host signaling pathways, including, but not limited to, the Hedgehog (Hh), the Bone Morphogenetic Protein (BMP), the Notch (N) signaling pathway and combinations thereof.

In certain embodiments, the compound is an antagonist or inhibitor that inhibits the Hedgehog signaling pathway, such Hedgehog inhibitor includes small molecule inhibitors, including but not limited to, cyclopamine or related chemical derivatives thereof, GOC-0449 (aka, Vismodegib (ERIVEDGE™), Genentech), IPI-926 (aka, SARIDEGID, Infinity Pharmaceuticals), LDE-225 (aka, Erismodegib, Novartis), LY2940680, Hh antagonist VIII, Hh antagonist XV, Gant 58, Gant 61, BMS-833923 (aka, EXELIXIS, Bristol-Myers Squibb), and any other Hedgehog signaling inhibitors now known or later developed. In certain embodiments, the Hedgehog inhibitor used for protection and/or treatment of influenza is cyclopamine.

As used herein, compounds and agents that are Hedgehog agonists or stimulators, or antagonists or inhibitors, include those that are well known in the art, and later discovered and developed by those skilled in the art. Examples of small molecule antagonists or inhibitors of the Hedgehog signaling pathway are disclosed, for instance, in Peukert and Miller-Moslin (2010, ChemMedChem 5: 500-512); Williams et al. (2003, PNAS 100(8): 4616-4621); and Tremblay et al. (2009, J. Med. Chem. 52(14): 4400-18, for IPI-926); Examples of protein antagonists or inhibitors of the Hedgehog signaling pathway are disclosed, for instance, in Brunton et al. (2008, J. Med. Chem. 51(5): 1108-1110). The entire contents of all of these references are incorporated by reference herein.

In other embodiments, the compound modulates the Bone Morphogenetic Protein (BMP) signaling pathway. As used herein, compounds and/or agents that are BMP agonists, antagonist, stimulators or inhibitors include those that are well known in the art, and later discovered and developed by those skilled in the art. Such BMP modulating compound includes, but is not limited to, Dorsomorphin, DMH1, LDN-193189. Examples of BMP inhibitors are disclosed, for instance, in Hao et al. 2008, PLoS One 3(8):e2904, for Dorsomorphin; and Axon Medchem Cat. No. 1509 for LDN-193189. The entire contents of these references are incorporated by reference herein. Examples of BMP agonist include, but are not limited to, BMP4 and TGF-beta.

In yet other embodiments, the compound modulates the Notch (N) signaling pathway, including, but not limited to, extracellular modulators which influence binding or activation of Notch by its ligands, cytoplasmic modulators, which influence signal transduction steps after receptor activation, and nuclear modulators, which influence the transcriptional activity of Notch-CSL protein complex, now known or later developed. Examples of Notch inhibitors include, but are not limited to, DAPT, DBZ, LY411575, L6885458, L852647, MK-0752, gamma-secretase inhibitors (GSI), Semagacestat, and RO4929097. Examples of Notch agonists include, but are not limited to, Delta-like-1 (D11-1), D11-2, D11-3 D11-4, Jagged, and activated intracellular domains of Notch receptors delivered to cross the plasma membrane and enter host cells including: Notch1, Notch2, Notch3, and Notch4.

As used herein, compounds and/or agents that are Notch (N) agonists, antagonist, stimulators or inhibitors include those that are well known in the art, and later discovered and developed by those skilled in the art. Examples of Notch signaling modulators are disclosed, for instance, in Panin & Irvine (1998). The entire contents of these references are incorporated by reference herein. Examples of the Notch modulator include, but are not limited to DAPT, DBZ, LY411575, L6885458, L852647, MK-0752, gamma-secretase inhibitors (GSI), Semagacestat, and RO4929097.

In certain embodiments, due to variances of influenza viral strains, the significant differences in NS1 activities and its associations with essential signaling pathways in different host species, such as invertebrates vs. vertebrates, the compound encompassed in the invention can be agonists, antagonists, inhibitors, or stimulators that modulate the Hh, BMP, or N signaling pathways, or any proteins or molecules involved in these signaling pathways, alone or in combination. Given the novelty of the present disclosure, it would be routine for one skilled in the art to select an appropriate agonist, antagonist, inhibitor, or stimulator in light of the particular activity of different NS1 viral protein in different viral strains associated with the Hedgehog (Hh), BMP, or Notch (N) signaling pathways in different host species and stages of infection.

In particular, mice infected with either the wild-type form of the mouse adapted PR8 virus or the A122V mutant variant of that virus can be treated with agonists or antagonists to each of these three pathways at different doses and mice can be assesed by various criteria including: signs of morbidity, damage to the lung epithelium (at various time points), cytokine production (at various time points), and lethality curves. Compounds reducing any of the above indices of infection can then be combined to determine the level of activity in concert to reduce disease pathology more effectively than either alone. Mixtures of inhibitors showing the greatest promise in mice can be routinely optimized for clinical trials in humans, particularly where any such compounds were not already clinically approved for other diseases (e.g., Hh antagonists for breast cancer and gamma secretase inhibitors for Alzheimer's Disease).

In certain embodiments, the invention provides that genetic epistasis experiments indicate that NS1 acts at the level of the transcriptional mediators of Hedgehog, Bone Morphogenetic Protein, or Notch signaling pathways. A point mutation in NS1 (A122V) was identified that impairs this activity. When the A122V mutation was incorporated into a mouse-adapted influenza A virus, it increased lung epithelial damage and hastened lethality. This epithelial damage was partially rescued by treating mice with the Hh antagonist cyclopamine. These results indicate that, in addition to its multiple intracellular functions, NS1 also modifies communication between host cells, which limits overall cell damage and lethality. The invention thus provides how this novel signaling function of NS1 is advantageous to the virus.

In certain embodiments, the invention provides that NS1 alters expression of Hh and N target genes by modulating activity of their transcriptional effectors (Ci/Gli and N-ICD respectively). This novel signaling activity remains unaltered by mutations in NS1 that block its interactions with other known host effectors. A novel point mutation in a surface residue of NS1 (A122V), however, does abrogate this signaling function. Incorporation of the A122V mutation into a mouse adapted influenza virus increases virulence, causing earlier death, increased morbidity, and greater lung pathology than the parental virus. In addition, treatment with the Hh inhibitor cyclopamine reduces viral damage in the lung. Therefore, the invention provides a new signaling function of NS1 that tempers influenza virulence and provides new therapeutic avenues for treating infection. Specifically, the invention further provides that modulating NS1 associated essential host signaling systems, such as the Hedgehog (Hh), the Bone Morphogenetic Protein (BMP), or the Notch (N) pathways, that are exploited by the pathogen is an effective approach to preventing and treating influenza viral infection.

In certain embodiments, the present invention provides that the NS1 protein from both highly virulent, as well as seasonal forms of influenza virus, activates a branch of the Hedgehog signaling pathway leading to increased expression of Bone Morphogenic Proteins ligands in *Drosophila*, although this effect varies considerably among different viral strains, suggesting that it is a characteristic that may be selected to determine viral fitness. The PR8 virus also induces BMP expression in lung epithelial cells in infected mice. The invention further provides that the NS1 protein interferes with Notch signaling pathway, as well, by altering Notch target gene expression in *Drosophila*. Accordingly, the invention provides that a compound, such as an antagonist or inhibitor of the Hedgehog (Hh) signaling pathway, an antagonist or inhibitor of the BMP signaling, or an modulator of the Notch (N) signaling, alone or in combination, could provide an effective treatment for various strains of influenza viral infection.

As used herein, the terms "compound," "pharmacologically active agent," "therapeutic agent," "active agent," or "drug" are used interchangeably to refer to a natural or synthetic chemical material, or biological material, that induces a desired pharmacological, physiological, biological effect, and include agents that are therapeutically or prophylactically effective. The terms also encompass pharmaceutically acceptable, pharmacologically active derivatives and analogs of those active agents specifically mentioned herein, including but are not limited to, salts, esters, amides, prodrugs, active metabolites, inclusion complexes, analogs, and the like. When the terms "compound," "pharmacologically or biologically active agent," "active agent," and "drug" are used, it is to be understood that applicants intend to include the active agent per se as well as pharmaceutically or biologically acceptable, pharmacological or biological active salts, esters, amides, prodrugs, active metabolites, inclusion complexes, analogs, etc., which may be collectively referred to herein as "pharmaceutically or biologically acceptable derivatives."

The pharmacologically agents as used herein may also refer to any oligonucleotides (antisense oligonucleotide agents), polynucleotides (e.g. therapeutic DNA), ribozymes, dsRNAs, siRNA, RNAi, gene therapy vectors, and/or vaccines for therapeutic use. The term "antisense oligonucleotide agent" refers to short synthetic segments of DNA or RNA, usually referred to as oligonucleotides, which are designed to be complementary to a sequence of a specific mRNA to inhibit the translation of the targeted mRNA by binding to a unique sequence segment on the mRNA. Antisense oligonucleotides are often developed and used in the antisense technology. The term "antisense technology" refers to a drug-discovery and development technique that involves design and use of synthetic oligonucleotides complementary to a target mRNA to inhibit production of specific disease-causing proteins. Virtually all diseases are associated with inadequate or over-production of proteins. Traditional small molecule drugs are designed to interact with disease-causing proteins and inhibit their function. In contrast, antisense technology permits design of drugs, called antisense oligonucleotides, which intervene at the genetic level and inhibit the production of disease-associated proteins. Antisense oligonucleotide agents are developed based on genetic information.

As an alternative to antisense oligonucleotide agents, ribozymes or double stranded RNA (dsRNA), RNA interference (RNAi), and/or small interfering RNA (siRNA), can also be used herewith as pharmaceutically active agents. As used herein, the term "ribozyme" refers to a catalytic RNA-based enzyme with ribonuclease activity that is capable of cleaving a single-stranded nucleic acid, such as an mRNA, to which it has a complementary region. Ribozymes can be used to catalytically cleave target mRNA transcripts to thereby inhibit translation of target mRNA. The term "dsRNA," as used herein, refers to RNA hybrids comprising two strands of RNA. The dsRNAs can be linear or circular in structure. The dsRNA may comprise ribonucleotides, ribonucleotide analogs, such as 2'-O-methyl ribosyl residues, or combinations thereof. The term "RNAi" refers to RNA interference or post-transcriptional gene silencing (PTGS). The term "siRNA" refers to small dsRNA molecules (e.g., 21-23 nucleotides) that are the mediators of the RNAi effects. RNAi is induced by the introduction of long dsRNA (up to 1-2 kb) produced by in vitro transcription, and has been successfully used to reduce gene expression in variety of organisms. In mammalian cells, RNAi uses siRNA (e.g. 22 nucleotides long) to bind to the RNA-induced silencing complex (RISC), which then binds to any matching mRNA sequence to degrade target mRNA, thus, silences the gene.

As used herein, a term "effective amount" refers to a quantity which results in a desired biological, therapeutic and/or prophylactic effect without causing unacceptable side effects when administered to a patient in need of the invention pharmaceutical composition. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a Hh, BMP, or N inhibitor for the prevention or treatment of influenza viral infection is the quantity that would result in greater control of symptoms associated with influenza viral infection than in the absence of the inhibitor.

A "effective amount" as used herein will also depend on the type and severity of the disease and on the characteristics of the subject, such as general health, age, sex, body weight and tolerance to drugs. The dose of the invention composition administering to a patient in need will depend on a number of factors, among which are included, without limitation, the patient's sex, weight and age, the type and/or severity of the disease, the route of administration and bioavailability, the pharmacokinetic profile of the agent, the potency, the formulation, and other factors within the particular knowledge of the patient and physician. Thus, it is not necessary to specify an exact effective amount herein. However, an appropriate effective amount in any individual case may be determined by one of ordinary skill in the art using routine experimentation. Furthermore, the exact effective amount of an active agent incorporated into a composition or dosage form of the present invention is not critical, so long as the concentration is within a range sufficient to permit ready application of the solution or formulation so as to deliver an amount of the active agent that is within a therapeutically effective range.

As used herein, the composition of the invention comprising a compound modulating at least one of the Hh, BMP, or N signaling pathways could be supplied in any pharmaceutically acceptable form, including in an oral, liquid, or tablet form, aerosolized for administration by inhalation, or formulated for parenteral administration such as in sealed sterile vials for intravenous administration to preventatively treat patients that are likely to have been exposed to influenza infection, or as a treatment to reduce the severity of infection for patients who are suspected or known to be infected by the virus. The composition of the invention can be used either alone or in combination with any existing pharmacologically active agents, including antiviral drugs, such as TAMIFLU, or other therapeutic agents known for preventing or reducing severity of influenza viral infection, or associated syndromes.

As used herein, solutions are homogeneous mixtures prepared by dissolving one or more chemical substances (solute) in another liquid such that the molecules of the dissolved substance are dispersed among those of the solvent. The solution may contain other pharmaceutically acceptable chemicals to buffer, stabilize or preserve the solute. Commonly used examples of solvents used in preparing solutions are saline, water, ethanol, propylene glycol or any other pharmaceutically acceptable vehicle.

A typical dose range for a therapeutic composition of the present invention will range from about 1 μg per day to about 5000 μg per day. Preferably, the dose ranges from about 1 μg per day to about 2500 μg per day, more preferably from about 1 μg per day to about 1000 μg per day. Even more preferably, the dose ranges from about 5 μg per day to about 100 μg per day. A person skilled in the art will take care to select the suitable effective amount of the invention composition, such that a desired therapeutic or prophylactic effect is obtained without causing unacceptable side effects when administered to a patient in need.

As used herein, the term "pharmaceutically acceptable carrier" refers to carrier materials suitable for administration of the compound, also referred to as a pharmaceutically active agent. Carriers useful herein include any such materials known in the art, which are nontoxic and do not interact with other components of the composition in a deleterious manner. Various additives, known to those skilled in the art, may be included in the composition of the present invention. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The pharmaceutically active agent may be administered through any desirable route, such as oral and/or any parental administration, if desired, in the form of a salt, ester, amide, prodrug, derivative, or the like, provided the salt, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by March's Advanced Organic Chemistry: Reactions, Mechanisms and Structure, 5th Ed. (Wiley-Interscience, 2001). Preparation of salts, ester, amides, prodrug, etc. is known to those skilled in the art or described in the pertinent literature.

The composition can be administered to a human. However, the invention composition can also be administered to any mammals including companion animals (e.g., dogs, cats, and the like), farm animals (e.g., cows, sheep, pigs, horses, chickens, and the like) and laboratory animals (e.g., rats, mice, guinea pigs, and the like).

The therapeutic candidates are compounds of any type. They may be of natural origin or may have been produced by chemical synthesis. They may be a library of structurally defined chemical compounds, of non-characterized compounds or substances, or a mixture of compounds. Various techniques can be used to test these compounds and to identify the compounds of therapeutic interest which modulate the Hedgehog, Bone Morphogenetic Protein, or Notch signaling pathways, or any molecules associated with these signaling pathways.

An in vivo screening method can be carried out in any laboratory animal, for example *Drosophila* or a rodent. In certain embodiments, the screening method comprises administering the test compound to the animal, then observing symptoms, sampling bodily fluids or tissues, analyzing tissue biopsy sample histologically, or optionally sacrificing the animal by euthanasia and taking a suitable biological sample before evaluating activities of the Hedgehog, Bone Morphogenetic Protein, or Notch signaling pathways, by any method described herein.

The invention may be understood more readily by reference to the following detailed description of the preferred embodiments of the invention and the Examples included herein. However, before the present peptides, compounds, compositions, and methods are disclosed and described, it is to be understood that this invention is not limited to specific compounds, specific peptides or proteins, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. It is also to be understood that as used in the specification and in the claims, "a" or "an" can mean one or more, depending upon the context in which it is used. Thus, for example, reference to "a cell" can mean that at least one cell can be utilized.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. These and many other variations and embodiments of the invention will be apparent to one of skill in the art upon a review of the appended description and examples.

EXAMPLES

A Novel Signaling Function of the Influenza NS1 Protein Provides Protection to the Host During Infection The NS1 protein produced by influenza A viruses suppresses host cellular defense mechanisms. The following examples provide a new role for NS1 in modifying cell-cell communication via two well characterized signaling pathways known as the Hedgehog (Hh) and Notch (N) pathways. Genetic studies indicate that NS1 alters the transcriptional read out of these pathways. A point mutation in NS1 (A122V) was identified that impairs this signaling activity. The A122V mutation was incorporated into a mouse-adapted influenza A virus and was found to increase lung epithelial damage and hasten lethality. This epithelial damage could be partially rescued by treating mice with the compound cyclopamine, which is an antagonist of the Hh pathway. These results indicate that, in addition to its multiple intracellular functions, NS1 also modifies communication between host cells, which limits overall cell damage and lethality caused by the virus and may optimize viral success by the host for future infection.

Example 1

Materials and Methods

Immunohistochemistry of Fly Wing Imaginal Discs

Generation of mitotic clones and immunohistochemistry was performed as previously described in (Smelkinson et al. 2007). Antibodies used are listed below.

Generation of Wild-Type and Recombinant Influenza Viruses

The influenza A/PR/8/34 (PR8; H1N1) wild type virus was rescued as previously described (Hoffmann et al. 2000). Alanine 122 in the PR8 NS1A protein was changed to valine using site-directed PCR mutagenesis of the PR8 NS gene, and the resulting DNA was cloned into a pol-II plasmid, pHH21. This mutation does not change the sequence of the NS2 protein. Viruses were amplified as described previously (Twu et al. 2006).

Immunohistochemistry of Mouse Lungs

Lungs were harvested at 2 dpi and placed in PBS-buffered formalin, blocked in paraffin, and 10-μm tissue sections were cut, and placed on glass slides. Sections were deparaffinized followed by antigen retrieval and antibody staining using standard methods.

Mouse Infections and Cyclopamine Treatment

C57BL/6 mice were infected intra-tracheally with A/PR/8/34; H1N1 viruses at $10^4$ PFU and monitored daily for morbidity for 14 days. Alternatively, mice were anesthetized with isoflurane and lungs dissected. Cytokine production was measured from lung homogenates by ELISA assay using DuoSet kits from R&D systems (R&D, Minneapolis Minn.). Cyclopamine and tomatidine were dissolved in a solution of 4:1 cyclodextran: ethanol (v:v) and 0.5 mg was administered as an intraperitoneal injection daily from 0-2 dpi. All infected mice were housed in biocontainment at the animal facility of TSRI. Quantification of viral titers in mouse lungs is described below.

Cloning and Site-Directed Mutagenesis cDNAs for *Drosophila* germline transformation and tissue-culture cell transfection were inserted into Gateway Technology vectors (Invitrogen). Point mutations were made with the QuikChange Site-Directed Mutagenesis Kit (Stratagene), and products were sequenced in their entirety before recombination into destination vectors.

Viral NS1 constructs: The cDNAs of NS1 from A/Vietnam/1203/04 (Vn; provided by Robert Webster), A/Udorn/72 (Ud), A/California/09 (Sw), and A/Puerto Rico/8/1934 (PR8) were inserted into pENTR-SD/TOPO (Invitrogen) via "topo cloning". The destination vector used for germline transformation into $w^{118}$ flies is pTFHWM, which contains pUASt regulatory elements and encodes both a composite N-terminal Flag/HA epitope tag and a C-terminal Myc epitope tag (modified from plasmids available at the DGRC). At least 3 individual *Drosophila* lines were analyzed for each transformed construct.

CPSF30 protein expression construct: An N-terminal fragment of CPSF30 encompassing four zinc finger domains (1-F4) was inserted in pENTR-SD/TOPO by "topo" cloning then recombined into destination vector, pcDNA-DEST40 (Invitrogen) which has a C-terminal V5 epitope tag and promoter elements required for expression in HEK293T cells.

NS1 protein expression construct: pGEX3X-NS1/Ud 1-215 was made as described in (Melen et al., 2007) for bacterial expression and purification of GST tagged NS1.

In Vitro GST Pull-Down Assay 200 ng of purified GST or GST-NS1(Ud) was bound to glutathione Sepharose beads in TBS+0.5% NP40 for 1 hr at 4° C. in a volume of 100 μl. Beads were washed twice and then incubated with 400 ul of a HEK293T cell lysate containing a V5 tagged N-terminal fragment of CPSF over night at 4° C. Beads were then washed three times and eluted with 2×SDS-PAGE loading buffer and boiled for 5 min prior to loading. Proteins were visualized by Western blotting with mouse anti-V5 (Invitrogen) and rabbit anti-GST primary antibodies. Alexaflour-488 and -647 were used as secondary antibodies and visualized with a Typhoon 9400 scanner.

Immunoblotting

Detection of NS1 from fly extracts: Flies carrying UAS-NS1 constructs were crossed to flies carrying a heat shock-GAL4 driver. 10 progeny flies were then heat shocked at 37° C. for 2 hours and allowed to recover for 1 hour. Flies were then homogenized in PBST, centrifuged, and supernatant recovered. SDS-PAGE loading buffer and reducing agent were then added to the supernatant and boiled for 5 minutes prior to loading on an SDS-PAGE gel. Following Western blotting, the NS1 protein was visualized with mouse anti-Myc (Sigma, 1:2000) and/or rabbi anti-HA (AbCam, 1:1000) antibodies. Alexaflour-488 and -647 were used as secondary antibodies and visualized with a Typhoon 9400 scanner.

Detection of viral proteins from infected tissue culture cells: A549 cells were grown in DMEM supplemented with 10% heat inactivated fetal bovine serum (FBS). Cells were infected with 5 plaque forming units (pfu/cell) of the indicated virus. After 1 hour of adsorption at 37° C., cells were washed once with PBS and replenished with DMEM containing 2% FBS and incubated at 37° C. for the indicated times. Cells collected at the indicated times after infection were lysed in RIPA buffer (50 mM Tris-HCl pH 7.5, 150 mM NaCl, 1% NP-40, 0.5% sodium deoxycholate, 0.1% SDS) supplemented with Complete® protease inhibitor (Roche). Immunoblots were probed using the following primary antibodies: rabbit antibody against the major structural proteins of the Ud virus, which detects the nucleocapsid (NP) and matrix (M1) proteins provided by Robert A. Lamb (Chen et al., 2007) and rabbit anti β-tubulin antibody (Cell Signaling).

Mouse Lung Immunohistochemistry

Lung sections were deparaffinized in 2 changes of xylenes for 5 minutes each and then hydrated in washes with ethanol followed by distilled water. Antigen retrieval was performed by immersing slides in a buffer containing 10 mM Tris pH 9.0, 1 mM EDTA, 0.05% Tween-20 and boiling for 30 minutes. Slides were allowed to cool for 20 minutes, rinsed in PBST, and then blocked in PBST+5% BSA for 1 hour. Sections were incubated in primary antibody overnight followed by 3 washes in PBST and incubation in an alkaline phosphatase conjugated secondary antibody for 1 hour. To perform the alkaline phosphatase reaction, sections were washed 3 times in alkaline phosphatase buffer (100 mM Tris, pH 9.5, 50 mM MgCl2, 100 mM NaCl, 0.1% Tween) and then incubated with NBT/BCIP substrates until staining could be visualized. Reaction was stopped by immersing slides in ethanol and tissue was mounted in Aqua-Polymount (Polyscience, Inc.).

Antibodies used for Immunohistochemistry of *Drosophila* Wing Discs and Mouse Lungs Primary antibodies used for staining *Drosophila* wing discs are mouse anti-beta-galactosidase 1:20 (DSHB), Rabbit anti phospho SMAD1 1:1000 (P. Ten Dijke), rabbit anti-myc 1:100 (Sigma), rabbit anti-Spalt 1:500 (Jose De Celis), mouse anti-patched 1:200 (DSHB), mouse anti-collier 1:100 (Crozatier), rat anti-Ci 2A1 1:2 (Holmgren), mouse anti en 1:5 (DSHB), and mouse anti cut 1:100 (DSHB). Alexaflour secondary antibodies (Invitrogen) were used at 1:1000. Antibodies used for mouse lung immunohistochemistry were goat anti-BMP2 (sc-6895; 1:50) and rabbit anti-goat-AP (Invitrogen; 1:100).

Quantification of Viral Titers in Mouse Lungs

Lungs were homogenized in MEM+0.1% bovine serum albumin (BSA) by bead beating. Homogenate was 10-fold serially diluted and 500 ul was added to MDCK cell monolayers in 6-well plates. Following incubation for 1 hour at 37° C., virus was removed and cells were overlaid with 3 ml of a 1:1 MEM:agarose solution containing 1 ug/mL TPCK-treated trypsin. After 48 hours, cells were fixed with 4% PFA and stained with a 0.1% solution of crystal violet and plaques were counted.

*Drosophila* Genetics and Screens

Fly crosses: dpp-lacZ, mtv-lacZ, or Gbe-lacZ (which contains several Su(H) promoter binding sites) expression in discs expressing NS1, was analyzed by crossing females with the genotype w; dpp-lacZ; 71B or w; dpp-lacZ; C765, or dpp-lacZ$^{EP}$; 71B; or ptc-GAL4; dpp-lacZ, or w; mtv-lacZ; 71B, or dpp-lacZ; 71B CiRNAi, or, w Gbe-lacZ; C765 to w; UAS-NS1 males or mutant variants. dpp-lacZ encodes the dpp disk enhancer described in (St Johnston et al., 1990). dpp-lacZ$^{EP}$ is an enhancer trap reporter of dpp expression. dpp expression was assayed in: 1) discs expressing components of the Hh, Dpp signaling pathways with or without NS1 by crossing females with the genotype UAS-Tkv or UAS-Tkv$^{DN}$ or UAS-Sog$^{CR1}$ UAS-PKA$^{act}$ or UAS-PKA$^{R}$ or UAS-smoD1-3 or UAS-Ptc or UAS-Ci$^{S849A}$ to males with the genotype w; dpp-lacZ; 71B or w; UAS-NS1 dpp-lacZ/CyO; 71B/TM6; 2) discs expressing Gli1 with or without NS1, by crossing females with the genotype w; dpp-lacZ; 71B or w; dpp-lacZ$^{EP}$/CyO; 71B/TM6B to males of the genotype w; UAS-Gli1/TM6B or w; UAS-NS1/CyO; UAS-Gli1/TM6B; 3) in fu mutant discs was analyzed by crossing females with the genotype ywhsflp fu$^{mH63}$; FRTDy+175[fu]/CyO; 71B/TM6B to males with the genotype yw; UAS-NS1; dpp-lacZ and y-males were selected; 4) in mtv mutant clones expressing NS1 was examined by crossing females of the genotype ywhsflp; FRT40Aubi-GFP; 71B to males of the genotype w; FRT40Amtv$^{6}$/CyO; UAS-NS1 dpp-lacZ; and 5) in kn mutant discs expressing NS1 by crossing females of the genotype w; kn$^{1}$; 71B to males with the genotype w; kn$^{1}$; UAS-NS1 dpp-lacZ. Finally, dpp expression dependent upon NS1 were analyzed with or without co-expression of Ci$^{S849A}$ in cos-2 mutant clones by crossing females of the genotype ywhsflp; 42Bubi-GFP; 71B dpp-lacZ to males of the genotype w; 42Bcos-2$^{2}$/CyO; UAS-NS1 or w; 42B cos-2$^{2}$/CyO; UAS-NS1 UAS-Ci$^{S849A}$. Cut expression was assayed in discs from a cross with females with the genotype UAS-NICD to males with the genotype C765 or UAS-NS1/CyO; C765/TM6B.

EMS mutagenesis of *Drosophila*: Male flies with the genotype w; UAS-NS1/CyO were starved for approximately 8 hours and then placed in a vial with a Kim-wipe adsorbed with 1.2 mL of a 0.26% EMS (Sigma) solution in 5% sucrose. The flies were allowed to feed on the EMS overnight and then crossed to females with the genotype w MS1096-GAL4. Transgenes from progeny displaying a revertant phenotype were sequenced and then verified by cloning the identified mutations into fresh UAS expression vectors and transforming them back into flies, thereby ruling out possible second site mutations.

Generation of a dominant negative form of NS1 in *Drosophila*: Flies carrying the UAS-NS1 transgene were crossed to flies carrying the Δ2-3 transpose, which induces P-element directed deletions and truncations. Progeny from this cross with the genotype UAS-NS1/CyO; Δ2-3 were then crossed to flies with the genotype MS1096; NS1 and suppression of the strong wing phenotype caused by expression of the wild type copy of NS1 were screened for in progeny. Candidate dominant negatives were then isolated, DNA extracted, and subjected to inverse PCR to determine the chromosomal location of the transgene. Primers directed to the N-terminus of the transgene and the neighboring genomic region were used to PCR amplify the truncated transgene which was then sequenced in its entirety.

Example 2

NS1 Alters a Branch of Hh Signaling in *Drosophila*

An NS1 cDNA from the Vietnam H5N1 viral strain (referred to as NS1(Vn)), double tagged with HA (N-terminus) and Myc (C-terminus) epitopes were expressed in the *Drosophila* wing by placing it under the transcriptional control of the yeast upstream activating sequence (UAS) (Brand and Perrimon 1993). Flies carrying this construct were crossed to strains expressing the yeast GAL4 transactivator protein in wing-specific patterns to conditionally activate expression of the UAS-NS1(Vn) transgene in the wings of progeny (FIG. 1B-D). Localized expression of NS1(Vn) in the central organizer (FIG. 1B) or ubiquitous expression throughout the wing (FIGS. 1C,D) increased the distance between the L3 and L4 veins in a dose-dependent fashion, a phenotype indicative of broadened Hh signaling (Biehs et al. 1998; Crozatier et al. 2002). Notches along the edge of the wing were also observed (arrows in FIGS. 1C,D) indicating that NS1 has additional non-Hh related effects, which may be mediated by the Wg or Notch signaling pathways (see below).

Consistent with its final wing phenotype, expression of NS1(Vn) in ubiquitous (FIG. 1F) or organizer specific (FIG. 1K) patterns greatly increased expression of a minimal synthetic dpp-lacZ reporter (St Johnston et al. 1990) along the A/P border in late larval wing discs. In contrast, expression of other Hh target genes, Ptc, Collier (Col), and Engrailed (En), was not appreciably altered by NS1(Vn) (FIGS. 5A,B,E,F,I, J), suggesting that its effect was limited to a specific branch of the Hh pathway (see below, however, regarding the more active NS1(PR8) form).

Figure 6:
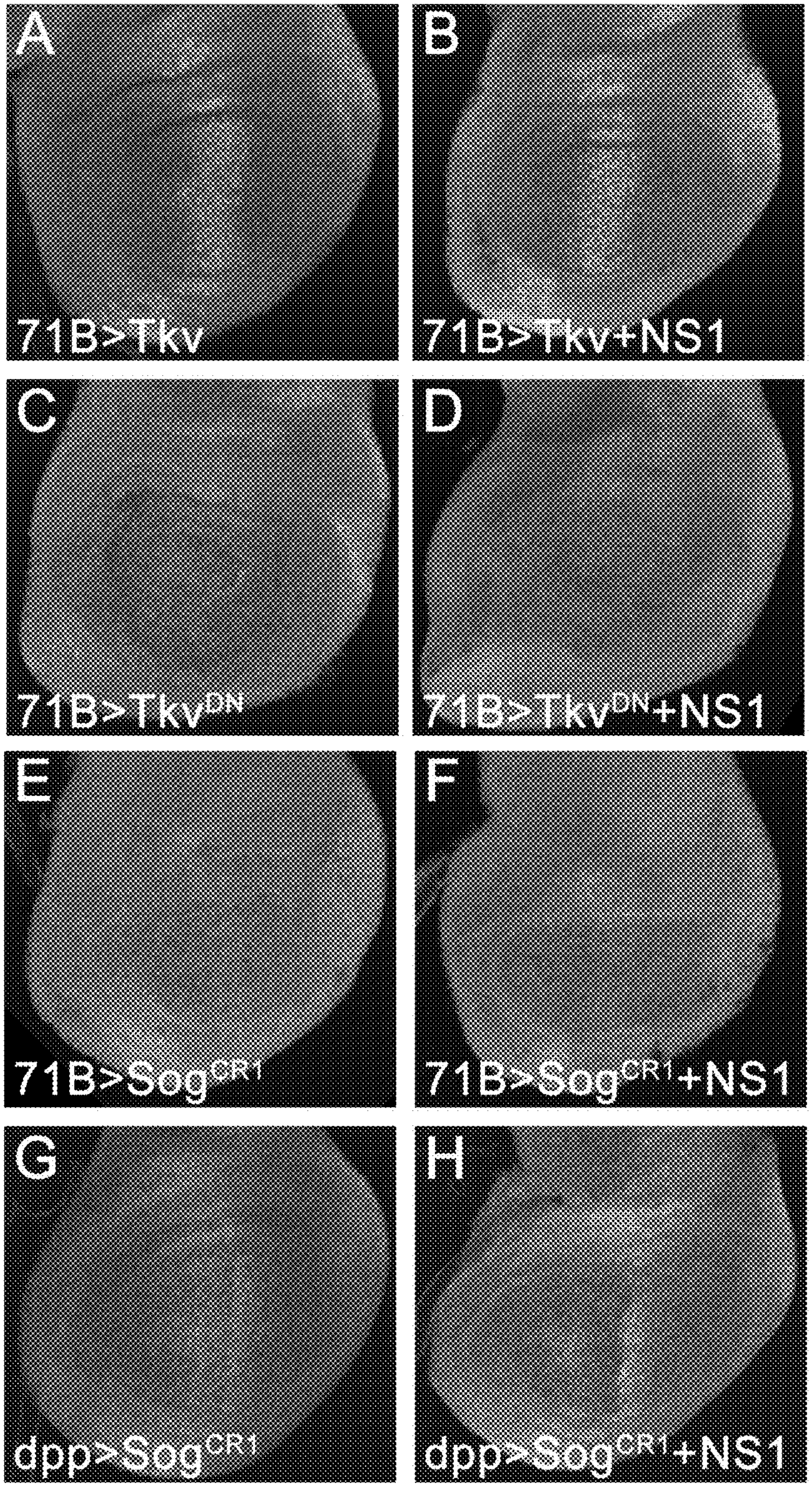
FIG. 6: Secreted Dpp mediates the non-autonomous effect of NS1 on neighboring cells. Wing discs expressing NS1 and indicated transgenes with the ubiquitous 71B-GAL4 driver (A-F), or along the A/P border with the dpp-GAL4 driver (G, H), were assayed for the pattern of Dpp response by staining with a phospho-Smad1 antibody. Ubiquitous expression of a wild-type form of the Dpp type-II receptor subunit Thick veins (Tkv) has little effect on NS1 activity (A, B), while expression of a dominant negative form of this receptor subunit eliminates both endogenous and NS1 activated pSMAD staining (C, D). Ubiquitous expression of the potent secreted SogCR1 Dpp antagonist (Yu et al., 2000) also results in strong reduction of the NS1 response (E, F), while A/P expression of SogCR down-regulates the response strongly in A/P border cells but seems to allow some signal to escape into adjacent regions, possibly owing to its expression levels being fairly low directly along the A/P border (G, H).

Dpp secreted from the central organizer diffuses to form a long range gradient extending both anteriorly and posteriorly (Affolter and Basler 2007), which can be detected in situ by staining for the phosphorylated (and active) form of the cytoplasmic signal transducer Mothers against decapentaplegic (pMAD) (Teleman and Cohen 2000) or Dpp target genes such as spalt (Nellen et al. 1996; Lecuit and Cohen 1998). Both ubiquitous (FIG. 1G-J) and central-organizer specific (FIGS. 1K, L) expression of NS1(Vn) in the wing disc broadened the domains of pMAD and Spalt staining indicating an expanded range of Dpp signaling. Consistent with a non-autonomous action of NS1(Vn) on adjacent cells, preventing diffusion of Dpp out of the central organizer abolished its BMP-inducing effect (FIG. 6).

NS1 activates Dpp signaling cell non-autonomously by promoting higher expression of dpp at the A/P border. One way to test for the non-autonomous effect of a factor that regulates BMP signaling is to determine whether it can alter the amount of free Dpp ligand diffusing into neighboring domains. Ubiquitous expression of the receptor, Tkv, inhibits Dpp diffusion and results in restricted activation of signaling in Dpp producing cells along the A/P border (FIG. 6A). As expected, when co-expressed NS1(Vn) with Tkv it was found that it enhanced Dpp signaling selectively along the A/P border (FIGS. 6A, 6B). Furthermore, co-expression of NS1(Vn) with a dominant negative form of Tkv or with the antagonist Short Gastrulation (Sog), a secreted protein that sequesters Dpp away from the receptor, completely blocked NS1-induced Dpp signaling and thus phosphorylation of Mad (FIGS. 6E-6H) (Nellen et al., 1996; Yu et al., 2000) (unpublished data). In contrast, NS1(Vn) retained the ability to enhance Dpp signaling in neighboring cells when Sog expression was restricted to the A/P border, a configuration that blocks Dpp activity locally, but allows (and possibly facilitates) Dpp diffusion (FIGS. 6G,6H). From these observations, it was concluded that NS1(Vn) increases long range Dpp signaling by increasing the level of dpp expression, and hence Dpp protein production, within Hh responding cells along the A/P border.

Example 3

Figure 2:
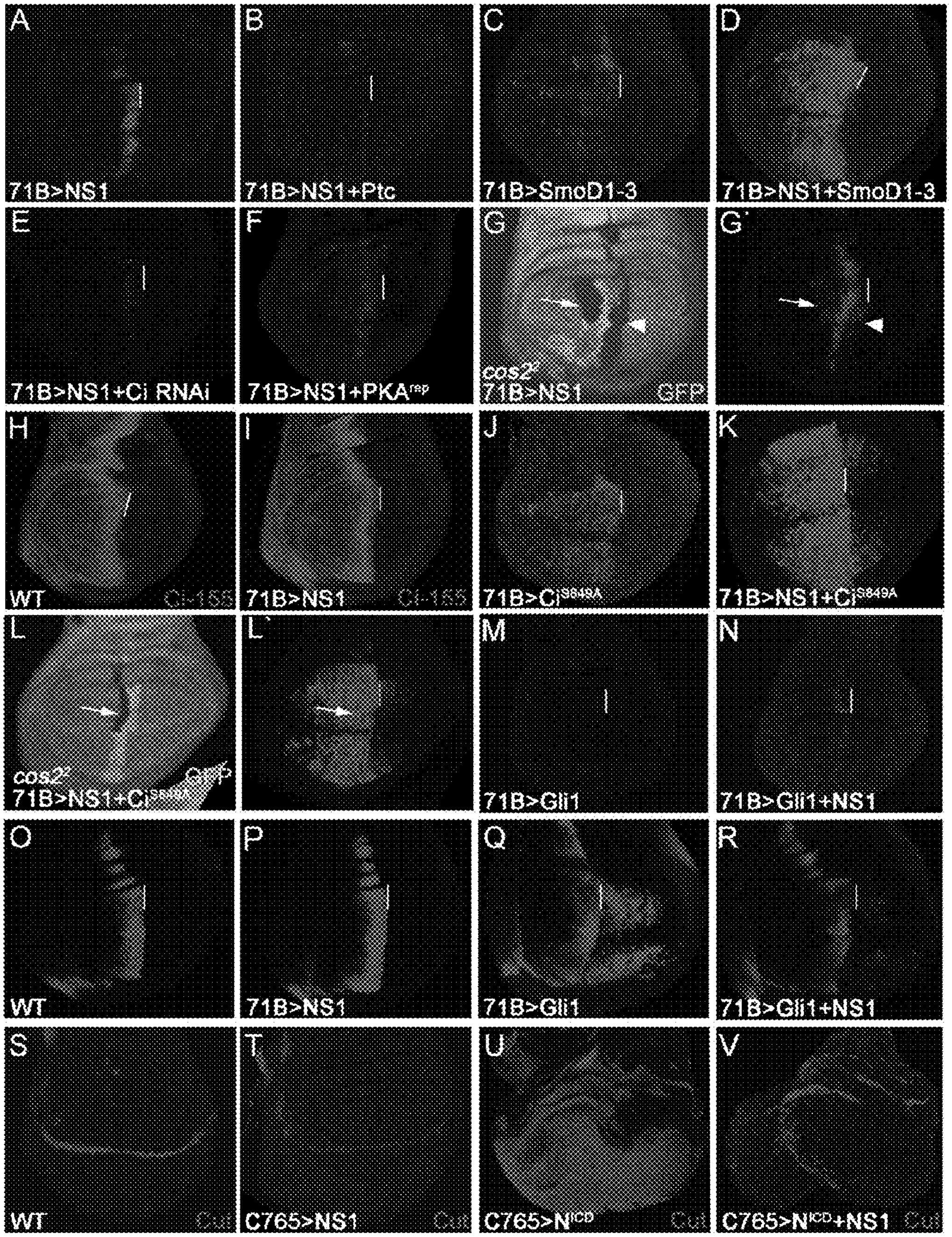
FIG. 2: NS1 alters the activity of *Drosophila* Ci and mammalian Gli1. Wing discs expressing the indicated transgenes driven by 71B-GAL4 were stained for dpp-lacZ (A-F, G', J, K, L', M,N), Ci-155 (H,I), or dpp-lacZ$^{EP}$ (0-R) expression. NS1 activation of dpp-lacZ expression (A) was suppressed by co-expression with the inhibitory Ptc co-receptor (B) and potentiated by ubiquitous expression the activated SmoD1-3 receptor (C,D). Coexpression of NS1 with a Ci RNAi construct blocked NS1 activation of dpp-lacZ expression(E). Co-expression of NS1 with the inhibitory regulatory subunit of PKA (PKA$^{rep}$) (F), or eliminating function cos 2 in mutant clones (lacking GFP in G) prevents NS1 from activating high levels of dpp-lacZ expression (G') in anterior (arrow) and A/P border cells (arrowhead). Ci-155 protein levels were similar in wild-type (H) and NS1-expressing (I) discs. NS1 enhanced $Ci^{S849A}$ mediated ectopic expression of dpp-lacZ (J,K). cos 2 mutant clones (lacking GFP and marked by an arrow in L) expressing activated $Ci^{S849A}$ do not reduce NS1-dependent induction of dpp-lacZ expression (L'). Ubiquitous expression of mammalian Gli-1 blocked both endogenous (M) and NS1 dependent (N vs. A) expression of dpp-lacZ. NS1-22 dependent activation of dpp-lacZEP expression (O vs. P) was also disrupted by co-expression with Gli1 (P vs. Q). Similarly, NS1 disrupted ectopic posterior activation of dpp-lac$Z^{EP}$ caused by ubiquitous expression of Gli1 (Q vs. R). Ubiquitous expression of NS1 using the C765-GAL4 driver also blocked expression of the N target gene Cut along the future wing margin (S vs. T) and similarly reduced Cut expression induced by ubiquitous expression of the activated N-ICD transcriptional effector (U vs. V).
Figure 7:
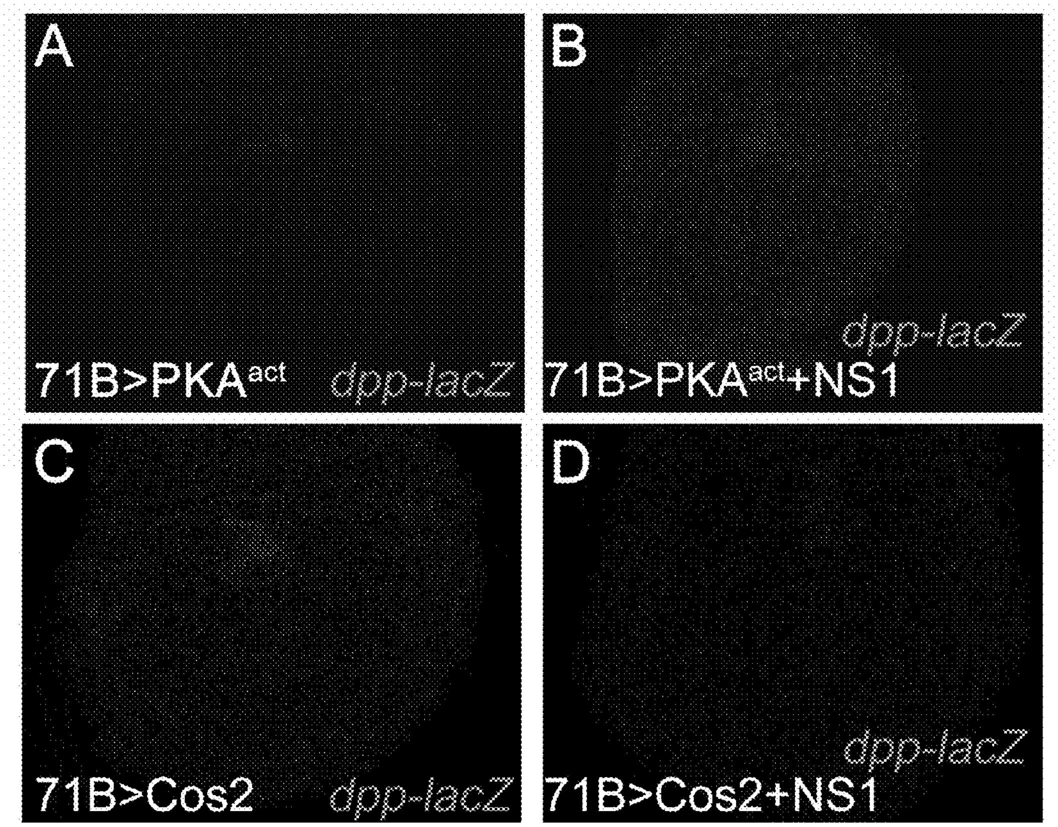
FIG. 7: Elimination of Ci-155 blocks NS1 activity. Ubiquitous expression of $PKA^{act}$ (B vs. A) or Cos-2 (D vs. C), which both greatly reduce levels of Ci-155 by promoting its proteolysis, blocked the ability of NS1 to activate dpp-lacZ expression.

NS1 Alters the Activity of Ci/Gli1 and Alters Notch Signaling at the Level of its Transcriptional Effector The effect of NS1 on the Hh pathway was examined. Overexpressing the Ptc receptor, which sequesters Hh thereby preventing it from diffusing into the anterior compartment (Chen and Struhl 1996; Biehs et al. 1998), blocked the ability of NS1(Vn) to upregulate dpp-lacZ expression (FIGS. 2A,B). Conversely, ectopic activation of Hh signaling in the anterior compartment by ubiquitously expressing a constitutively active phosphomimetic form of Smoothened potentiated NS1(Vn) activity throughout this region (FIGS. 2C,D). These results indicate that NS1(Vn) activity is Hh-dependent. To determine whether NS1 requires the presence of the full-length form of the transcriptional effector Ci (Ci-155), Ci-155 levels were reduced by RNA-interference (FIG. 2E) or NS1 (Vn) was co-expressed with either the active catalytic subunit of PKA ($PKA^{act}$) or Cos-2 (FIGS. 7C,D), both of which promote proteolysis of Ci-155 to the Ci-75 repressor form. In each case NS1(Vn) activity was abolished, demonstrating a requirement for Ci-155 in this process.

Figure 8:
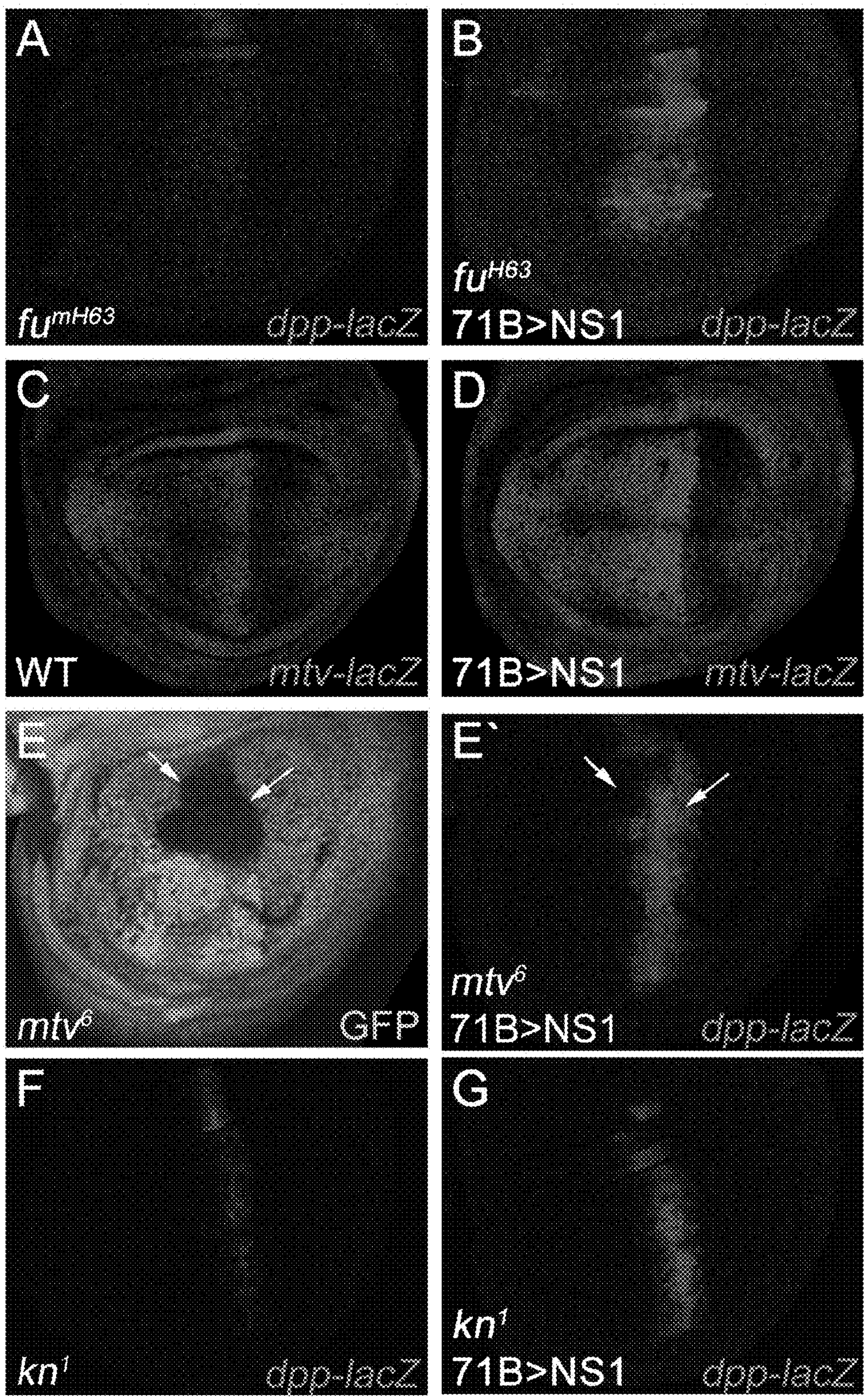
FIG. 8: Ci target genes, mtv and kn, do not mediate NS1-dependent dpp activation. In fused (fu) mutant discs, dpp-lacZ expression is broadened but not elevated (A). Expression of NS1 in a fu mutant background can potentiate dpp-lacZ expression throughout the expanded response zone (B), indicating that fu is not required for the dpp-activating function of NS1, although Fused is required for full activation of Ci-155. mtv-lacZ expression in wild type discs (C) and discs ubiquitously expressing NS1(Vn) with the 71B-GAL4 driver (D). NS1(Vn) can enhance mtv-lacZ expression at the A/P border and activate expression throughout a broad domain in the anterior compartment. In clones of cells expressing a strong hypomorphic allele of mtv, $mtv^6$, marked by the absence of GFP in (I) and marked by arrows in (E) and (E') high NS1-dependent expression of dpp-lacZ is unaffected (E'). In discs expressing a hypomorphic allele of kn, $kn^1$, expression of the dpp-lacZ reporter construct is not significantly altered in wing discs (F), nor is the ability of NS1(Vn) to elevate expression of this reporter (G).

Full length Ci-155 requires additional modification(s) from the Hh signaling pathway for full activity ($Ci^{act}$) (Hooper and Scott 2005). To determine whether NS1(Vn) required such Ci activation, NS1(Vn) was co-expressed with the inhibitory regulatory subunit of PKA ($PKA^{rep}$, FIG. 2F) or in clones of cells lacking function of Cos-2 (FIGS. 2G,G'), both of which block Ci phosphorylation thereby stabilizing Ci-155. Under these conditions, Hh signaling is also disabled due to required positive roles of both PKA and Cos-2 in transducing the signal (Wilson and Chuang 2010). In these experiments, despite the presence of abundant Ci-155, NS1 (Vn) was unable to fully activate dpp-lacZ expression. Thus, Ci-155 is required, but not sufficient, for NS1(Vn) activity as additional positive input from Hh signaling being is essential for its full effect (see FIG. 8 for further analysis). Consistent with NS1 affecting the specific activity of Ci, the levels and patterns of full length Ci expression were similar in wild-type and NS1(Vn) expressing discs (FIGS. 2H,I). In further support of NS1 acting in conjunction with $Ci^{act}$, co-expression of NS1(Vn) with a non-cleavable variant of Ci-155, $Ci^{S849A}$ (Smelkinson et al. 2007), which is active independent of Hh signaling, strongly enhanced dpp-lacZ expression throughout the disc (FIGS. 2J,K). This effect of NS1 extended well beyond the domain of Hh signaling, and did so even in the absence of cos-2 function (FIGS. 2L,L'). It thus concluded that NS1 interacts with fully-activated $Ci^{act}$, which is normally present along the A/P border where Hh signaling is high.

It was also examined whether Gli1, the mammalian transcriptional activator homologous to Ci (Huangfu and Anderson 2006; Wilson and Chuang 2010), would similarly mediate the response to NS1(Vn). In contrast to Ci, Gli1 nearly abolished the low basal expression of the synthetic dpp-lacZ reporter (FIG. 2M vs. FIG. 1E) and also blocked the ability of NS1(Vn) to augment its expression (FIG. 2N vs. 2A). Similarly, Gli1 prevented NS1(Vn) from fully activating expression of the more strongly expressed dpp-$lacZ^{EP}$ enhancer trap reporter along the A/P border (FIGS. 2O,P vs. 2Q). Gli1, which has previously been shown to be active only in posterior and A/P border cells, where Hh levels are high (Marks and Kalderon 2011), induces expression of dpp-$lacZ^{EP}$ in this domain (FIG. 2Q). This activity of Gli1 was reduced by NS1 (FIG. 2R vs. 2Q). Thus, NS1 and Gli1 consistently interact in an antagonistic fashion.

NS1 alters Notch signaling at the level of its transcriptional effector. As mentioned above, in addition to modulating Hh signaling, NS1 has a prominent effect of generating of notches along the wing margin (FIGS. 1C,D). Since Notch plays a central role in establishing the D/V border of the wing, expressions of various downstream Notch target genes were examined. It was found that expression of one such target, Cut, was greatly reduced (FIGS. 2S,T). Ubiquitous expression of the constitutively active N-ICD transcriptional cofactor in the wing primordium leads to a corresponding ectopic pattern of Cut expression (FIG. 2U) and this effect of N-ICD can also be greatly suppressed by NS1 (FIG. 2V). Thus, as in the case of the Hh pathway, NS1 alters Notch signaling at the level of its transcriptional effector.

Example 4

NS1 Activity is Independent of Fused Kinase, Knot, and Master of Thickveins and the Hh Modulating Effect of NS1 is not Mediated by Known Host Effectors Fused kinase (Fu) is required for converting Ci-155 into an active yet labile transcription factor, which may be the form that interacts with NS1 (Ohlmeyer and Kalderon, 1998; Zhou and Kalderon, 2011). Whether Fused is required for NS1 activity was tested by expressing NS1 in fused mutant wing discs and analyzed dpp-lacZ expression (FIGS. 8A, 8B). NS1 still augmented dpp-lacZ expression in these fused mutant discs indicating that Ci is activated by NS1 by a fused-independent pathway.

There is evidence that Hh, acting via Ci activation of Knot/Col, induces expression of master of thick veins (mtv), a gene that can modulate the Dpp response at the A/P border (Crozatier et al., 2002; Funakoshi et al., 2001). mtv, encodes a transcription factor that represses expression of the Dpp receptor, Tkv, reducing further the normal low level of Dpp signaling at the A/P border. Since, it has been demonstrated that elimination of Dpp signaling can increase dpp expression (Haerry et al., 1998) and because expression of mtv-lacZ, like dpp-lacZ, is increased by NS1(Vn) (FIGS. 8C, 8D), it was examined whether NS1 activation of dpp expression was a consequence of a reduction in Dpp signaling mediated by Knot/Col and/or Mtv. NS1(Vn) was expressed in discs mutant for kn or in clones of cells mutant for mtv (FIGS. 8E-8G). It was found that NS1(Vn) was still able to upregulate the expression of dpp-lacZ, providing that the ability of NS1(Vn) to augment dpp expression is independent of the Knot/Col/Mtv pathway auto-regulatory circuit. The absence of input from the Fused and Knot/Col/Mtv pathways suggest that NS1 acts by regulating the activity of $Ci^{act}$ itself (i.e., by directly and/or indirectly changing its specific activity).

The Hh modulating effect of NS1 is not mediated by known host effectors. NS1 binds to several known host effectors via specific interaction surfaces. Mutations have been identified in NS1 that selectively abrogate specific interactions with dsRNA or with its various host target proteins (all of which have homologues or closely related genes in *Drosophila*) (Hale et al., 2008). Host factors inhibited by binding to the NS1 ED include: protein kinase R (PKR), which halts cellular and viral protein synthesis; the 30 kDa subunit of cleavage and polyadenylation specificity factor (CPSF30) and poly(A)-binding protein II (PABII), which are required for mRNA maturation; and components of the nuclear export machinery (NXF1, p15, and Rae1) (Hale et al., 2008). The NS1 ED can also bind to the p85β regulatory subunit of phosphoinositide 3-kinase (PI3K) and, in some strains, Crk/CrkL which may act to stimulate proliferation and reduce apoptosis in virally-infected cells (Hale et al., 2008). In addition, residues spanning both the RBD and ED of NS1 have been implicated in temporal regulation of vRNA synthesis and selective translation of viral mRNAs (Hale et al., 2008).

Whether the NS1-dependent induction of dpp expression was due to an interaction with any of these known host factors by mutating the residues essential for those interactions and expressing the mutated transgenes in flies (Table 1). With only one exception (ds-RNA binding), none of these mutations altered dpp expression or pMAD staining. Mutations abolishing dsRNA-binding did reduce NS1 activity as well as protein levels in several lines. However, higher level of expression of such NS1 mutant transgenes had similar effects to the wild-type NS1 and was able to stimulate dpp-lacZ expression when co-expressed with activated $Ci^{S849A}$. It was conclude that the Hh inducing activity of NS1(Vn) is not mediated by host effectors that bind to previously identified NS1 interaction surfaces.

TABLE 1

Single and multiple amino acid mutations made in different strains of NS1

| Known mutations | dpp-lacZ expression | Adult Phenotype | Reason for change | Ref |
|---|---|---|---|---|
| Vn WT | ++++ | ++++ | | |
| Vn and Ud R38A** | + | + | Eliminates dsRNA binding | [1] |
| Vn G184R | ++++ | ++++ | Eliminates binding to CPSF30 | [2] |
| Vn I123A, M124A | ++++ | ++++ | Eliminates binding to PKR | [3] |
| Vn P164A, P167A | ++++ | ++++ | Eliminates binding to the p85β subunit of PI3K | [4] |
| Vn P210A | ++++ | ++++ | Mutation of SH3 domain, binding site to Crk family proteins in some strains | [5] |
| Vn Splice site mutant | ++++ | ++++ | Eliminates NEP fragment | |
| Vn A122V | + | + | Identified in EMS screen | |
| Vn A122I | + | + | Bulkier, hydrophobic residue at 122 | |
| Vn A122S | ++(+) | ++(+) | Hydrophilic residue at position 122 | |
| Vn L105W | +++(+) | ++(+) | Bulkier, hydrophobic residue at 105, on protein surface near A122 | |
| Vn L105S | ++++ | ++++ | Hydrophilic residue at 105, on protein surface near A122 | |
| Vn A122V, L105W | + | + | Combine mutations at 105 and 122 | |
| Vn M106F | +++ | ++++ | Bulkier, hydrophobic residue at 106, on protein surface near A122. Also a CPSF30 binding site | |
| Vn M106S | ++++ | ++++ | Hydrophilic residue at 106, on protein surface near A122 | |
| Vn M106I, F98S | ++++ | ++++ | Changed to PR8 residues, on | |

TABLE 1-continued

Single and multiple amino acid mutations made in different strains of NS1

| Known mutations | dpp-lacZ expression | Adult Phenotype | Reason for change | Ref |
|---|---|---|---|---|
| | | | protein surface near A122 | |
| Vn D125E, D189G | ++++ | ++++ | Changed to Swine residues, on protein surface near A122 | |
| PR8 WT | ++++++++ | No adults | | |
| PR8 A122V | +++++ | +++++ (escapers) | Verify A122V also reduces PR8 effect | |
| PR8 I106M | ++++++++ | No adults | Changed to Vn residues, on protein surface near A122 | |
| PR8 I106A | ++++++++ | +++++++ (escapers) | Changed to A as to avoid binding to CPSF30 | |
| PR8 I106M, A122V | +++++ | +++++ (escapers) | Combined mutations at 106 and 122 | |
| PR8 I106A, A122V | +++++ | +++++ (escapers) | Combined mutations at 106 and 122 | |
| Swine WT | + | + | | |
| Sw R108K, I111V, V117I | + | + | Changed to Vn residues, near A122 | |
| Sw R108K, I111V, V117I, E125D, G189D | + | + | Changed to Vn residues, near A122 | |

Table Legend: Constructs with the indicated mutations in NS1 were expressed in fly wings and evaluated for enhancement of dpp- lacZ expression and adult wing phenotypes. Phenotypic strength is indicated by the number of "+"s. The rationale for the changes and citations, where available, are also listed.
**See Supplemental text for further characterization of NS1 R38A mutant.

[1]. Donelan, N. R., C. F. Basler, and A. Garcia-Sastre, *A recombinant influenza A virus expressing an RNA-binding-defective NS1 protein induces high levels of beta interferon and is attenuated in mice.* J Virol, 2003. 77(24): p. 13257-66.
[2]. Nemeroff, M. E., et al., *Influenza virus NS1 protein interacts with the cellular 30 kDa subunit of CPSF and inhibits 3'end formation of cellular pre-mRNAs.* Mol Cell, 1998. 1(7): p. 991-1000.
[3]. Min, J. Y., et al., *A site on the influenza A virus NS1 protein mediates both inhibition of PKR activation and temporal regulation of viral RNA synthesis.* Virology, 2007. 363(1): p. 236-43.
[4]. Shin, Y. K., et al., *SH3 binding motif 1 in influenza A virus NS1 protein is essential for PI3K/Akt signaling pathway activation.* J Virol, 2007. 81(23): p. 12730-9.
[5]. Heikkinen, L. S., et al., *Avian and 1918 Spanish influenza a virus NS1 proteins bind to Crk/CrkL Src homology 3 domains to activate host cell signaling.* J Biol Chem, 2008. 283(9): p. 5719-27.

Example 5

Figure 3:
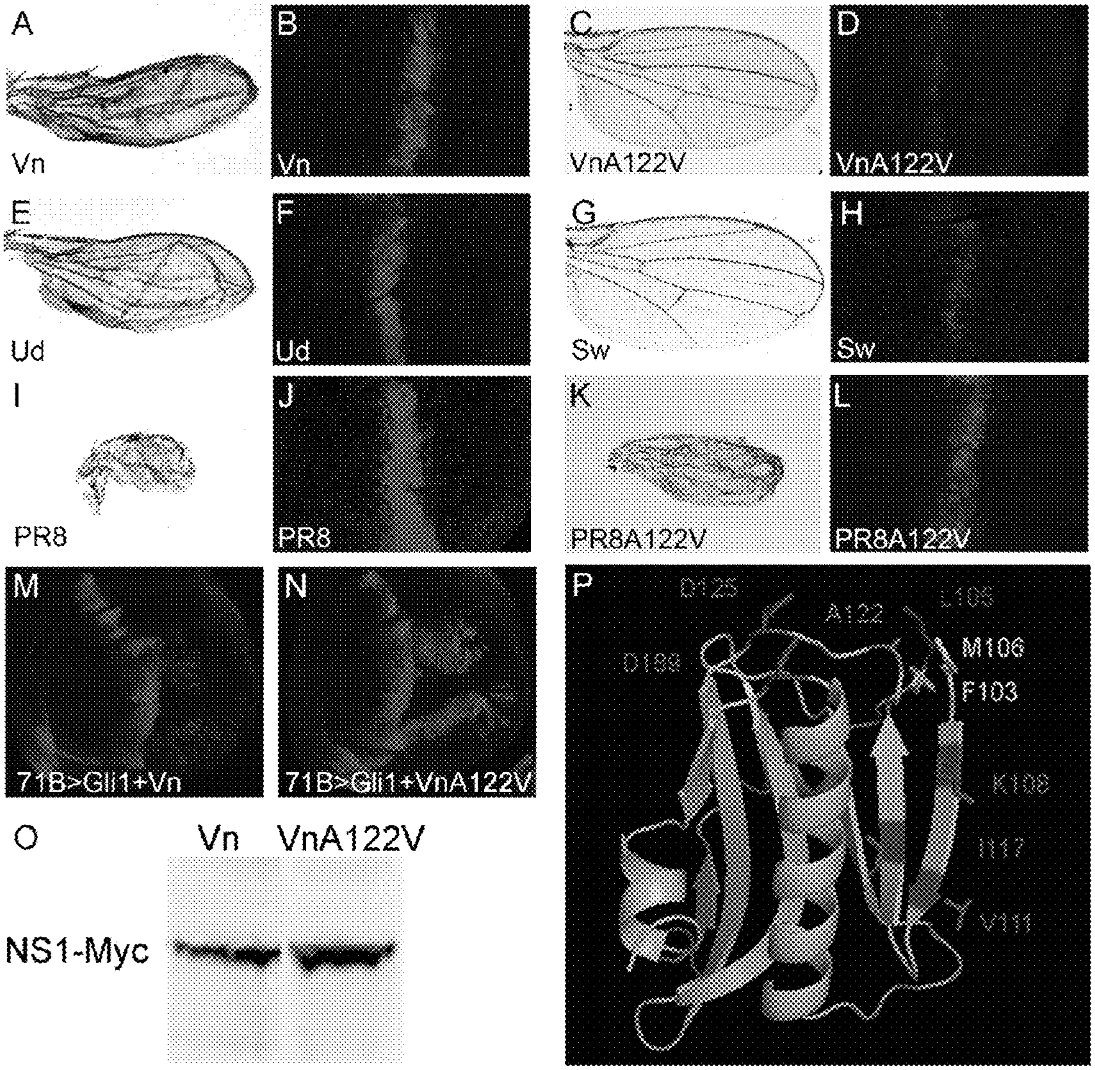
FIG. 3: A point mutation in NS1 reduces its ability to activate dpp-lacZ expression NS1 transgenes were expressed in adult wings with the strong MS1096-GAL4 driver (A, C, E, G, I, K) or in dpp-lacZ expressing wing discs with the moderate 71B-GAL4 driver (B, D, F, H, J, L). The NS1(Vn) phenotype (A,B) was greatly reduced by the A122V mutation (C,D). NS1(Ud) has a phenotype similar to NS1(VN) (E,F), whereas NS1(Sw) has weaker (G,H) and NS1(PR8) stronger (I,J) activity. The NS1(PR8) phenotype is significantly reduced by the A122V mutation (K,L). Silencing of Gli1-dependent ectopic activation of dpp-lacZEP by NS1(Vn) (M) is abolished by the A122V mutation (N). (O) Equivalent expression levels of the NS1(A122V) and original wild-type NS1 proteins were detected on Western blots using an antibody to C-terminal Myc tags. (P) Structure of the ED of NS1(Vn) displaying the position of A122 (magenta), L105 (blue), and surface residues altered in NS1(Sw) (red), or NS1(PR8) (cyan) (see Supp. Table 1 for results).

Structural Features of Amino Acid Residue A122 of NS1 and its Requirement for the Signal Modulating Activity Mutations in NS1 residues that abrogate its interactions with known host effectors did not compromise its activity in the *Drosophila* wing (Table 1), nor did co-expression of NS1 with candidate effectors such as PI3K or polyA binding protein (data not shown). An unbiased mutagenesis screen was therefore conducted to isolate new mutant alleles of NS1 that could no longer perform this signaling function. One revertant allele recovered had greatly reduced NS1 activity without affecting NS1 protein levels (FIG. 3O). This NS1 mutant carried an alanine to valine substitution at position 122 (A122V) (FIGS. 3C,D vs. 3A,B), a highly conserved residue mapping to the surface of the ED (FIG. 3P).

Substitutions of other amino acids at position 122 indicate that a key feature of the alanine residue is likely to be the small size of its side chain (Table 1). Structural features of the amino acid at position 122 essential for mediating the Hh modulating activity of NS1 were explored. A change from alanine to valine is rather subtle with the latter having only a slightly builder side group, yet remaining hydrophobic. To test whether the size of the side group was critical, NS1(Vn) transgenes were expressed in the wing with residues of different size and/or hydrophobicity incorporated into position 122. Isoleucine, a hydrophobic residue with an even bulkier side group than valine, gave a similar phenotype as A122V (Table 1). In contrast, a transgene with serine at this position, which is bulky yet hydrophilic, did not greatly compromise NS1 function (Table 1). These results suggest that a small hydrophobic residue at this position is most important feature for mediating the Hh modulating activity of NS1 and that bulkier, hydrophobic residues (i.e. Val or Ile) may sterically block this binding interface.

The A122V mutation also blocked the ability of NS1(Vn) to prevent Gli1-mediated activation of dpp-lacZ$^{EP}$ expression (FIG. 3M vs. 3N compare to FIGS. 2Q,R), suggesting that the A122 residue is critical for interacting with Hh pathway effectors across species. In addition, the A122V mutation reduced the effect of NS1 on Notch signaling targets (FIG. 9), suggesting that the same NS1 interaction surface engages both Hh and N transcriptional effectors.

Example 6

NS1 Activity Varies Significantly Between Viral Strains

Because different strains of influenza can differ dramatically in virulence, the Hh modulating activity of NS1 was examined in several viral strains including the standard seasonal Udorn virus, NS1(Ud), the recently emerged swine flu NS1(Sw), and the murine adapted PR8 virus, NS1(PR8). NS1 transgenes from these strains were expressed with a strong wing specific driver in order that even low levels of Hh inducing activity could be detected. NS1(Ud) produced wing phenotypes similar to those of NS1(Vn) (FIGS. 3E,F), while NS1(Sw) was significantly weaker (FIGS. 3G,H). NS1(PR8) was substantially stronger than NS1(Vn) (FIGS. 3I,J), but this activity was also reduced by the A122V mutation (FIGS. 3K,L). Since A122V is conserved between these strains, mutations in other surface amino acids close to A122 that differed between high versus low activity forms of NS1 were made to identify residues that may contribute to NS1 activity (FIG. 3P and Table 1). These experiments revealed that no individual or combination of residues contributed significantly to the variable activity between strains, suggesting that multiple amino acids, possibly encompassing different regions, contribute incrementally to the activity of NS1.

Example 7

Highly Active NS1(PR8) Affects a Broader Range of Hh Targets than NS1(Vn)

Figure 5:
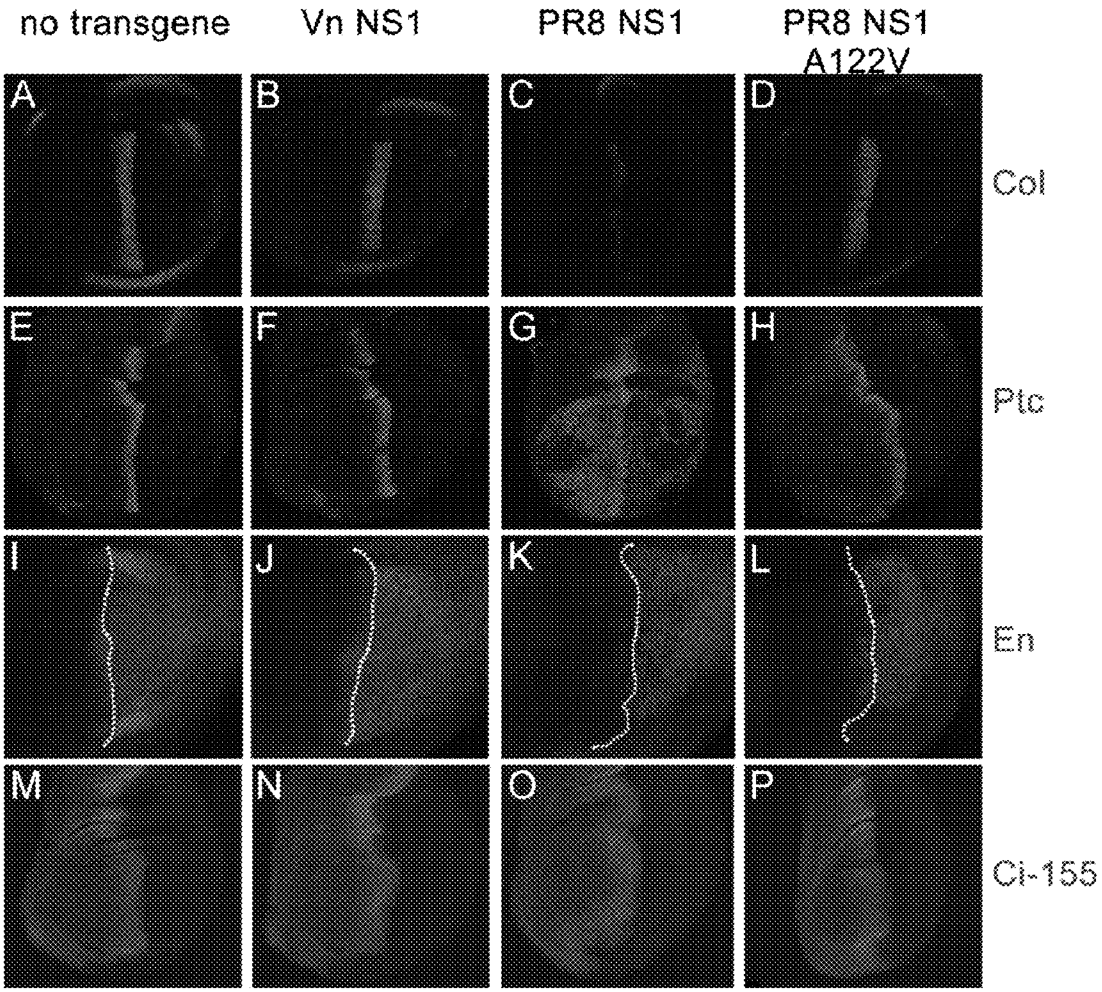
FIG. 5: Effects of Vn versus PR8 NS1 on other Hh target genes. Wing imaginal discs expressing the indicated transgenes were stained with antibodies recognizing Collier (Col) (A-D), (Ptc) (E-H), Engrailed (En) (I-L), and Ci-155 (M-P). White lines in I-L denote the A/P border. The moderately active Vn NS1 has little if any effect on expression Col (A,B); Ptc (E,F); or En expression (I,J)—note that En expression advances a short distance into the anterior compartment in late third instar wing discs (I,J); or full length Ci (M,N). The more strongly active PR8 NS1, however, results in reduced expression of Col (C, vs. A), anterior and posterior expansion of expression of Ptc but a reduction at the A/P (G vs. E), and reduced anterior expression of En (K vs. I). Each of these PR8 effects is greatly attenuated by the A122V mutation (C,D; G,H; K,L) indicating that all of these effects on Hh target genes are likely to be mediated by the same effector interaction as that involved in dpp-activation by both Vn and PR8 NS1. Similar to Vn, PR8 does not appreciably alter Ci-155 levels (O,P).
Figure 9:
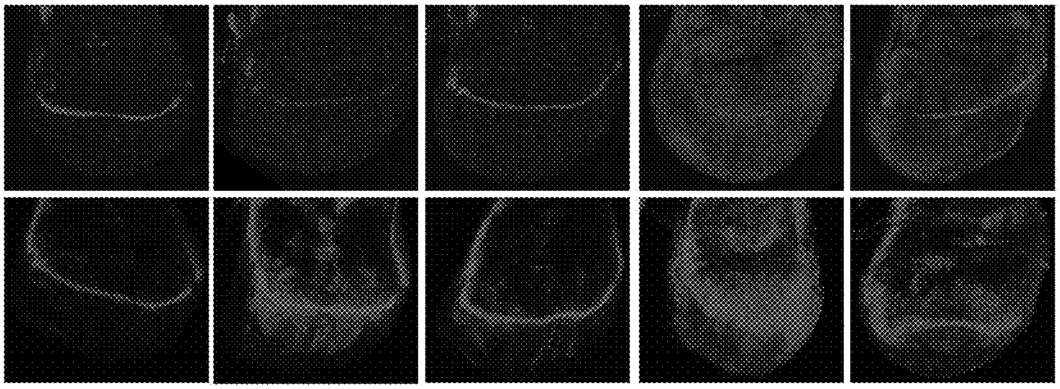
FIG. 9: NS1 alters Notch target gene expression in a strain specific and A122V-dependent fashion. NS1 (Vn) reduces expression of Cut along the presumptive wing margin (B vs. A) and increases expression of Gbe-lacZ, a synthetic Notch reporter gene construct (G vs. F). Both of these effects of NS1 (Vn) are greatly reduced by the A122V mutation (C vs. B and H vs. G). The effect of NS1 (PR8) is stronger than NS1 (Vn) with regard to Cut repression (D vs. B) and Gbe-lacZ activation (I vs. G), and both of these effects are reduced by the A122V mutation (E vs. D and I vs. J respectively).

As described above, among the viral strains tested, NS1 (PR8) was the most active. In addition, NS1(PR8) altered expression of Hh target genes that appeared unaffected by NS1(Vn) (e.g., Col, Ptc, and a narrow anterior En domain) (FIGS. 5C,G,K). These NS1(PR8)-specific effects included increased (e.g., dpp-lacZ FIG. 3J, Ptc—FIG. 5G) as well as decreased (e.g., Col, and En, FIGS. 5C,K) target gene expression. As was true for NS1(Vn), NS1(PR8) did not affect the levels or distribution of Ci-155 protein (FIG. 5M-P), providing further evidence that NS1 alters the specific activity of Ci rather than its protein stability/level. NS1(PR8) also had a stronger and broader range of activity than NS1 (Vn), which involved both repression (Cut) and activation (Gbe-lacZ reporter) of Notch target genes (FIG. 9). The differences between NS1(PR8) and NS1(Vn) notwithstanding, incorporation of the A122V mutation into NS1(PR8) reversed its effects on all Hh and N target genes, indicating that this single amino acid is critical for both the positive and negative effects of NS1 across strains (FIG. 3I-L; FIGS. 5D,H,L; FIGS. 9E,J).

Example 8

The NS1 A122V Mutation Increases Influenza Virulence in Mice

Figure 10:
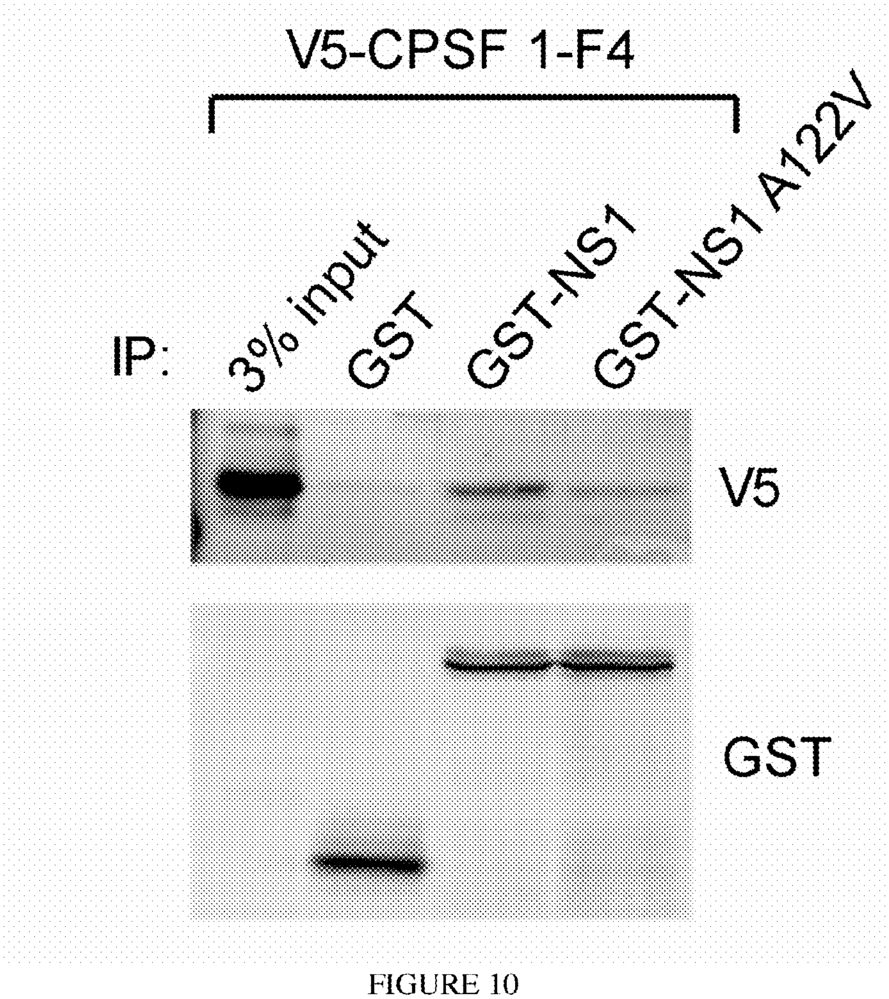
FIG. 10: The A122V mutation disrupts Udorn NS1 binding to CPSF30. GST or GST-NS1 fusion proteins were incubated with extracts of 293T cells transfected with an N-terminal fragment of CPSF30 containing four of its zinc finger binding domains and tagged C-terminally with a V5 epitope. Proteins immune precipitated with glutathione beads were visualized on Western blots with anti-V5 (top) and anti-GST (bottom) antibodies. The A122V mutation reduces NS1 binding to CPSF30 under these in vitro binding conditions. Note, however, that mutations of another known residue required for NS1 binding to CPSF30, G184, did not disrupt the dpp activating function of NS1 in *Drosophila* wing discs. These findings indicate that for in vivo infectivity experiments in mammals it is important to use a viral strain such as PR8 for which the activity of NS1 is independent of its ability to bind CPSF30.

Since the A122V mutation greatly reduced all signal modulating activities of NS1, its in vivo effect was also tested in a murine infection model. The PR8 virus was used for these experiments since NS1(PR8) is highly active and because PR8 virulence is independent of CPSF30 binding by NS1, a requirement for suppression of cellular mRNA maturation in other strains (Twu et al. 2006; Kochs et al. 2007). This latter fact was important since the A122V mutation in NS1(Ud), presumably due to its proximity to the CPSF30 binding site at M106, reduced this binding interaction (FIG. 10) (however, that mutations of M106 or G184 which selectively eliminate CPSF30 binding did not alter NS1(Vn) activity in *Drosophila*—Table 1).

Figure 11:
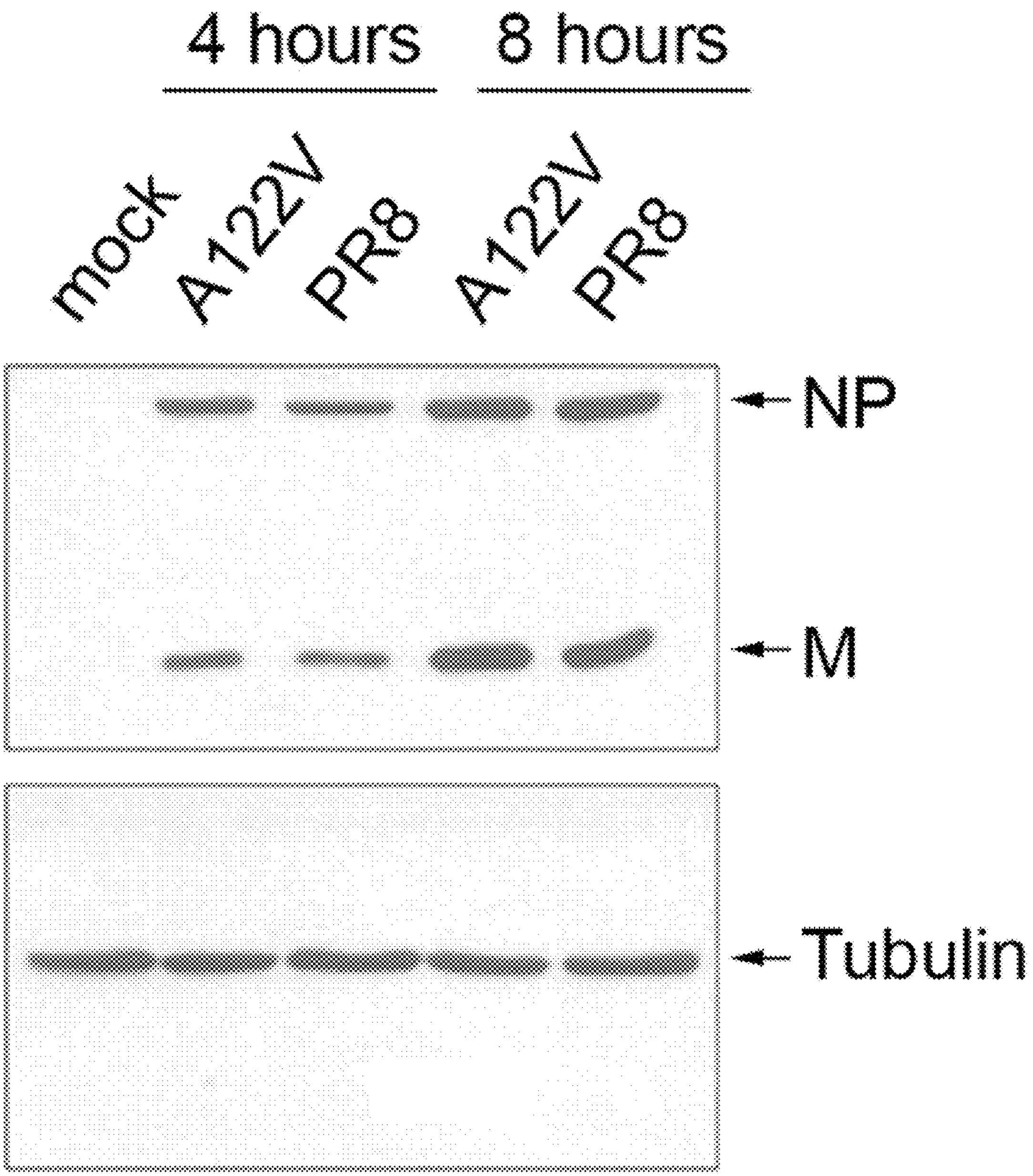
FIG. 11: The A122V mutation does not affect temporal regulation of viral proteins in infected tissue culture cells. Temporal synthesis of two viral proteins NP and M was examined in A549 cells following a high-MOI single cycle infection with the PR8 and PR8(A122V) viruses. No differences in the levels or kinetics of these markers were observed indicating that the A122V mutation does not alter temporal regulation of viral gene expression.

Based on the above considerations, parallel stocks of the parental PR8 and the PR8-A122V mutant viruses were prepared and infected sibling mice. Both viruses established comparable infection as assessed by viral titers in lungs and the range of tissues infected in mice at either two or four days post infection (FIG. 4A and data not shown), and displayed similar temporal regulation of viral genes in cell culture (FIG. 11). The NS1 A122V mutation does not alter temporal regulation of influenza genes. It was considered the possibility that PR8-A122V accelerates activation of the viral gene expression program since A122 lies in a region of NS1 that has been implicated in temporal regulation of viral gene expression (Min et al., 2007). It was found no differences, however, in the levels of the influenza NP or M proteins produced in A549 human lung epithelial cells infected with the wild-type versus PR8-A122V viruses 4 or 8 hours post infection (FIG. 11). It was concluded that temporal regulation of viral genes is unaltered by A122V, and thus is not the cause for the hastened lethality in PR8-A122V infected mice.

Figure 4:
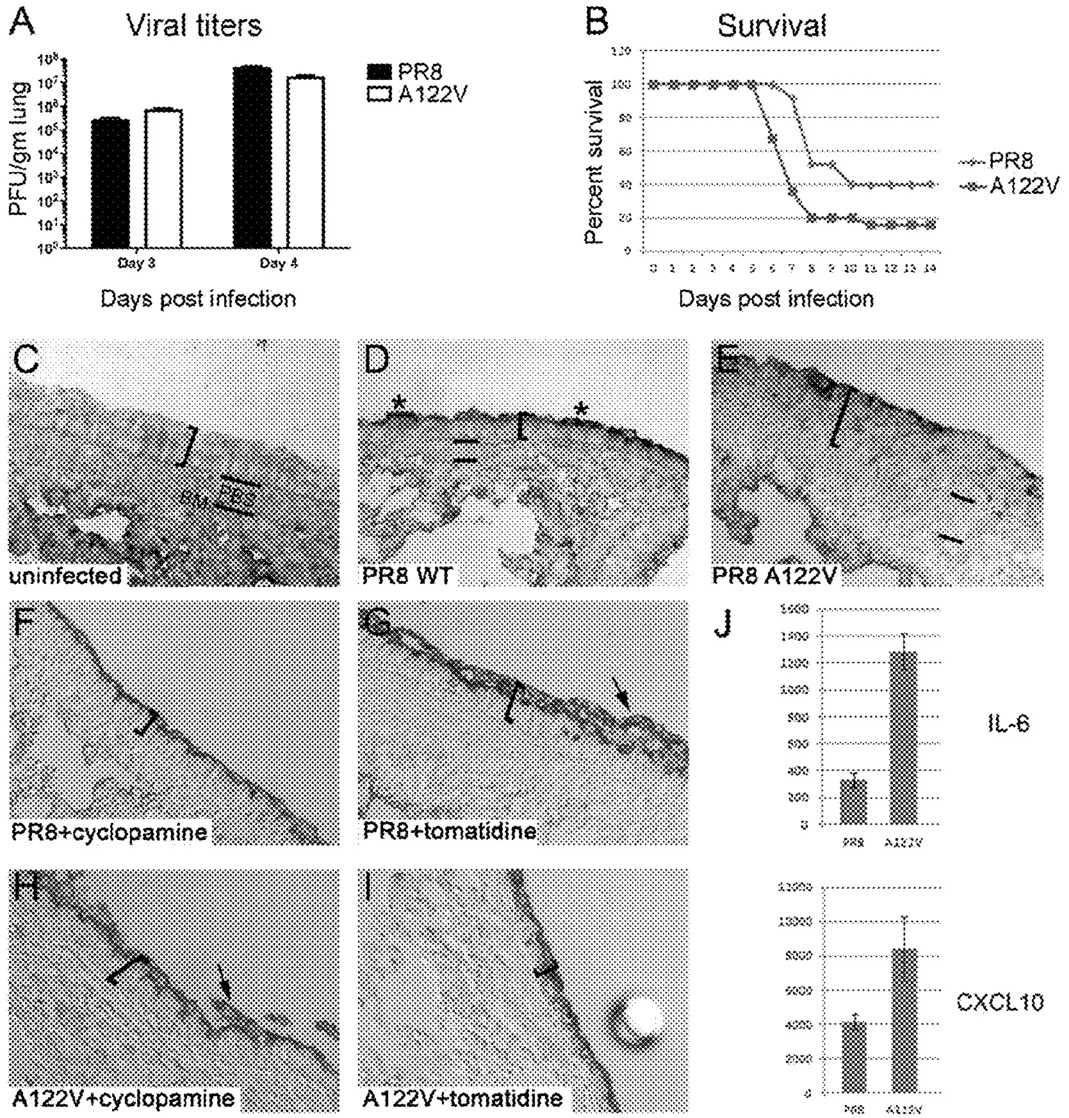
FIG. 4: NS1 A122V increases influenza pathogenesis in mice which can be partially rescued by treating with a Hh antagonist. (A) Similar viral titers were measured for mouse lungs infected with the PR8-WT and PR8-A122V viruses at 3 and 4 days post infection (dpi). (B) 25 mice per group compiled from three independent experiments were infected with either the PR8-WT (blue) or PR8-A122V viruses (red) at 1×104 pfu and monitored daily for survival (survival difference: $p<0.0001$). (CE) BMP2 expression and airway epithelial morphology in infected versus control major lung bronchioles. (C) In uninfected lungs, regular rows of columnar epithelial cells surrounded the major bronchioles (brackets) and express little, if any, BMP2. (D) The columnar epithelium in PR8-WT infected lungs was moderately disorganized and high levels of BMP2 expression were observed in some areas (asterisks). (E) The columnar epithelial layer was almost completely absent in PR8-A122V mutant virus infected lungs and the peribronchiolar space was enlarged (compared the distance between lines in E to C and D). (F-I) Mice were treated with a Hh signaling antagonist, cyclopamine (F,H), or an inactive analogue, tomatidine (G, I), from 0-2 dpi with either the PR8-WT or PR8-A122V viruses. Cyclopamine reduced epithelial damage caused by both PR8-WT (F) and PR8-A122V (H) while tomatidine had no obvious effect (arrow in G). BM=basement membrane (BM), PBS=peribronchial space (PBS) is indicated with lines. In C-I, the columnar epithelial layer is shown with a brackets. (J) Cytokine levels (pg/ml) in homogenates of PR8-WT (n=5) and PR8-A122V (n=4) virus infected lungs at 4 dpi. IL-6: $p<0.005$; CXCL10: $p<0.04$.

However, the PR8-A122V virus significantly hastened lethality of mice compared to the parental PR8 (PR8-WT) strain in several independent experiments (FIG. 4B, $p<0.0001$). PR8-A122V also induced greater signs of morbidity by 3 days post-infection (e.g., reduced mobility, hunched posture, labored breathing, and pilo-erectus—data not shown), indicating that the mutant virus is considerably more pathogenic than the parental strain.

PR8-A122V causes greater damage to the airway epithelium than PR8-WT. Lungs from both PR8-WT and PR8-A122V infected mice displayed obvious defects in the epithelial layer surrounding the major bronchioles compared to uninfected control littermates. This airway barrier, which is the primary site at which influenza initiates infection, is normally comprised of an organized row of columnar epithelial cells and an underlying smooth muscle layer (FIG. 4C). The columnar organization of this epithelial layer was disrupted by both viruses at two days post-infection, but PR8-A122V (FIG. 4E) caused significantly greater disorganization and cell sloughing than PR8-WT (FIG. 4D). Furthermore, the peribronchial space where cytokine secreting immune cells congregate upon infection (FIG. 4C-E, parallel lines), was enlarged in the PR8-A122V infected lungs relative to uninfected or PR8-WT infected lungs, indicative of a heightened immune response. Consistent with these morphological defects, the levels of several cytokines, in particular IL-6 and CXCL10 (FIG. 4J and data not shown), were significantly elevated in animals infected with PR8-A122V relative to PR8-WT, albeit some factors, such as TNF-α and IL-1β did not respond differentially to the two viruses (data not shown). The greater virulence of PR8-A122V relative to PR8-WT is therefore likely to be a consequence of the greater damage it inflicts on the airway epithelium, which may include a contribution of the host inflammatory response.

Example 9

Blocking Hh Signaling Decreases Lung Damage During Influenza Infection

Whether the damage observed in influenza infected lungs involved the Hh signaling pathway was further investigated. The expression of BMP2, the mammalian homologue of *Drosophila dpp*, was examined in infected airways, and found that it was strongly upregulated in epithelial cells infected with PR8-WT compared to uninfected controls, which may be expected as Hh signaling is part of the immune response (Crompton et al. 2007) (FIGS. 4C,D). BMP2 staining was also detected in PR8-A122V infected airways. To determine whether inhibiting Hh signaling might alter parameters of infection, animals were treated systemically with the potent Hh antagonist cyclopamine. It was found that cyclopamine reduced epithelial damage caused by both PR8-WT and PR8-A122V, and restored a degree of columnar organization to the epithelium (FIGS. 4F, H). In contrast, tomatidine, an inactive analogue of cyclopamine, provided no rescue of airway damage (FIGS. 4G, I). These findings suggest that Hh signaling contributes to the severity of damage inflicted by the virus.

Example 10

Identification of Novel Signaling Effects of NS1

The present invention identified novel cell non-autonomous effects of NS1 on Hh and N signaling in the *Drosophila* wing, which act at the level of the transcriptional effectors (Ci/Gli1 and N-ICD respectively) of these pathways. The effects of NS1 on Hh or N targets genes were either positive or negative depending on the particular target gene and NS1 strain, although in the case of mammalian Gli1, NS1 had a consistently inhibitory effect. The positive versus negative effects of NS1 on particular target genes may reflect promoter specific interactions in which the presence of NS1 can either stabilize or disrupt important interactions between transcription factors and other transcriptional machinery. Importantly, all effects of NS1 were greatly reduced by a single amino acid substitution (A122V), while mutations abrogating interactions with several known host effectors involved in viral replication or suppression of the interferon response had little if any effect on the signaling function of NS1. These observations suggest that a novel shared interaction surface of NS1 mediates its effects on components of transcriptional effector complexes.

Working Model for NS1 Activity in Mice

When the A122V mutation was introduced into the NS1 gene of the mouse adapted PR8 virus, it increased pathogenicity by accelerating death, increasing indices of morbidity, and producing greater damage to the airway epithelium relative to the parental wild-type (WT) strain. Mice treated with the Hh antagonist cyclopamine, but not a related inactive compound, were partially protected from the effects of influenza infection. To account for these various findings the following working model was provided: 1) as in flies, NS1 inhibits Hh-dependent Gli1 activity; 2) by inhibiting Hh signaling, which is part of the innate host defense system, NS1 or cyclopamine protects the host from potentially overly exuberant immune responses that could lead to deadly cytokine storms (see below); 3) by tempering its virulence via NS1 interfering with signaling through the Hh, N, and possibly other signaling pathways, the influenza virus optimizes its overall fitness by ensuring that the population through which it propagates remains intact.

The Hh and N Signaling Pathways are Potential Targets of Influenza

The Hh and N signaling pathways are plausible targets for manipulation by pathogens. In the case of Hh, this pathway has been shown to play an integral role in the immune response (Crompton et al. 2007). An overly-robust immune response, or cytokine storm, characterized by an uncontrolled positive feed-back loop between immune cells and cytokine production, is thought to have been a cause of many fatalities during the past influenza pandemics (de Jong et al. 2006; Kobasa et al. 2007; Cilloniz et al. 2009). It is possible that the hastened lethality that occurs in A122V virus infected animals is similarly due to an unrestrained immune response unleashing such cytokine storms. Indeed, levels of several cytokines were significantly higher in animals infected with PR8-A122V relative to PR8-WT, suggesting influenza could be able to limit the occurrence of such uncontrolled host responses via NS1 thereby improving host prognosis.

Decreasing Hh or N signaling by influenza may also limit damage to the infected tissue. Hh signaling has been shown to be induced in the lung by damage caused by chemical agents and many types of ailments (Stewart et al. 2003; Fisher et al. 2005; Pogach et al. 2007). Furthermore, expression of the Hh receptor, Ptc, is induced on infiltrating and circulating lymphocytes suggesting that immune cells are primed to respond to the Hh ligand secreted from the inflamed area (Stewart et al. 2003). These studies suggest a key role for Hh in repairing damaged lung tissue by remodeling the epithelium through or in conjunction with activated immune cells. However, too much remodeling by overactive signaling pathways (e.g. Hh, Wnt, PI3K, and TGF-β) can lead to the formation of detrimental fibrotic tissue (Selman et al. 2008). In the case of influenza infection, Hh can be activated to help repair the damaged lung epithelium, but its restricted activation by NS1 may prevent tissue fibrosis. Similar to what is shown for the affect of influenza on the lung, blocking Hh signaling with potent antagonists can often limit the extent of damage in other distressed tissue types as well (Pereira Tde et al. 2010; Philips et al. 2011; Horn et al. 2012).

N signaling has also been implicated in several aspects of innate and adaptive immunity forming an important bridge between antigen presenting cells and T-cell activation circuits (Ito et al. 2012). Indeed, increased expression of the Notch ligand Delta-like 1 (Dll1) has been observed in macrophages following challenge with influenza virus. Interestingly, this viral induced upregulation of Dll1 was protective to the host in that manipulations that reduced expression of this Notch ligand enhanced mortality during infection (Ito et al. 2011).

In conclusion, the data provides an example of a virus taking adaptive measures to diminish its virulence to sustain host viability. This action of NS1 is reminiscent of the well-known Australian effort to curb the levels of their imported rabbit population by infecting them with myxoma virus. While this virus initially decimated the rabbit population, animal numbers soon rebounded, albeit not to their prior levels. It has been suggested that this population equilibration is due to a combination of increased host resistance and reduced viral virulence relative to the original infecting strain, although the precise host and/or viral genes involved in this process have not been elucidated (Stanford et al., 2007). Thus, well adapted viruses may tune their virulence during the course of establishing a stable homeostatic relationship with their hosts, as could be the case for influenza A via its strain-specific interactions with the host Hh and N signaling pathways.

REFERENCES

1. Affolter M, Basler K (2007) The Decapentaplegic morphogen gradient: from pattern formation to growth regulation. Nat Rev Genet 8(9): 663-674.
2. Baskin, C. R., H. Bielefeldt-Ohmann, A. Garcia-Sastre, T. M. Tumpey, N. Van Hoeven, V. S. Carter, M. J. Thomas, S. Proll, A. Solorzano, R. Billharz, J. L. Fornek, S. Thomas, C. H. Chen, E. A. Clark, K. Murali-Krishna, and M. G. Katze. 2007. Functional genomic and serological analysis of the protective immune response resulting from vaccination of macaques with an NS1-truncated influenza virus. J Virol 81:11817-11827.
3. Biehs B, Sturtevant M A, Bier E (1998) Boundaries in the *Drosophila* wing imaginal disc organize vein-specific genetic programs. Development 125(21): 4245-4257.
4. Bier E (2005) *Drosophila*, the golden bug, emerges as a tool for human genetics. Nat Rev Genet 6(1): 9-23.
5. Bier E, Guichard A (2012) Deconstructing host-pathogen interactions in *Drosophila*. Dis Model Mech 5(1): 48-61.
6. Brand A H, Perrimon N (1993) Targeted gene expression as a means of altering cell fates and generating dominant phenotypes. Development 118(2): 401-415.
7. Chen, B. J., Leser, G. P., Morita, E., and Lamb, R. A. (2007). Influenza virus hemagglutinin and neuraminidase, but not the matrix protein, are required for assembly and budding of plasmid-derived virus-like particles. J Virol 81, 7111-7123.
8. Chen Y, Struhl G (1996) Dual roles for patched in sequestering and transducing Hedgehog. Cell 87(3): 553-563.

9. Cilloniz C, Shinya K, Peng X, Korth M J, Proll S C et al. (2009) Lethal influenza virus infection in macaques is associated with early dysregulation of inflammatory related genes. PLoS Pathog 5(10): e1000604.
10. Crompton T, Outram S V, Hager-Theodorides A L (2007) Sonic Hedgehog signalling in T-cell development and activation. Nat Rev Immunol 7(9): 726-735.
11. Crosby L M, Waters C M (2010) Epithelial repair mechanisms in the lung. Am J Physiol Lung Cell Mol Physiol 298(6): L715-731.
12. Crozatier M, Glise B, Vincent A (2002) Connecting Hh, Dpp and EGF signalling in patterning of the *Drosophila* wing; the pivotal role of collier/knot in the AP organiser. Development 129(18): 4261-4269.
13. de Jong M D, Simmons C P, Thanh T T, Hien V M, Smith G J et al. (2006) Fatal outcome of human influenza A (H5N1) is associated with high viral load and hypercytokinemia. Nat Med 12(10): 1203-1207.
14. Dufraine J, Funahashi Y, Kitajewski J (2008) Notch signaling regulates tumor angiogenesis by diverse mechanisms. Oncogene 27(38): 5132-5137.
15. Fisher C E, Ahmad S A, Fitch P M, Lamb J R, Howie S E (2005) FITC-induced murine pulmonary inflammation: CC10 up-regulation and concurrent Shh expression. Cell Biol Int 29(10): 868-876.
16. Fortini M E (2009) Notch signaling: the core pathway and its posttranslational regulation. Dev Cell 16(5): 633-647.
17. Funakoshi, Y., Minami, M., and Tabata, T. (2001). mtv shapes the activity gradient of the Dpp morphogen through regulation of thickveins. Development 128, 67-74.
18. Garcia-Sastre A, Egorov A, Matassov D, Brandt S, Levy D E, Durbin J E, et al. Influenza A virus lacking the NS1 gene replicates in interferon-deficient systems. Virology. 1998; 252(2):324-30.
19. Haerry, T. E., Khalsa, O., O'Connor, M. B., and Wharton, K. A. (1998). Synergistic signaling by two BMP ligands through the SAX and TKV receptors controls wing growth and patterning in *Drosophila*. Development 125, 3977-3987.
20. Hai, R., L. Martinez-Sobrido, K. A. Fraser, J. Ayllon, A. Garcia-Sastre, and P. Palese. 2008. Influenza B virus NS1-truncated mutants: live-attenuated vaccine approach. J Virol 82:10580-10590.
21. Hale B G, Randall R E, Ortin J, Jackson D (2008) The multifunctional NS1 protein of influenza A viruses. J Gen Virol 89(Pt 10): 2359-2376.
22. Hoffmann E, Neumann G, Kawaoka Y, Hobom G, Webster R G (2000) A DNA transfection system for generation of influenza A virus from eight plasmids. Proc Natl Acad Sci USA 97(11): 6108-6113.
23. Hooper J E, Scott M P (2005) Communicating with Hedgehogs. Nat Rev Mol Cell Biol 6(4): 306-317.
24. Horn A, Kireva T, Palumbo-Zerr K, Dees C, Tomcik M et al. (2012) Inhibition of Hedgehog signalling prevents experimental fibrosis and induces regression of established fibrosis. Ann Rheum Dis.
25. Huangfu D, Anderson K V (2006) Signaling from Smo to Ci/Gli: conservation and divergence of Hedgehog pathways from *Drosophila* to vertebrates. Development 133 (1): 3-14.
26. Hughes T T, Allen A L, Bardin J E, Christian M N, Daimon K et al. (2012) *Drosophila* as a genetic model for studying pathogenic human viruses. Virology 423(1): 1-5.
27. Irvine K D, Vogt T F (1997) Dorsal-ventral signaling in limb development. Curr Opin Cell Biol 9(6): 867-876.
28. Ito T, Connett J M, Kunkel S L, Matsukawa A (2012) Notch system in the linkage of innate and adaptive immunity. J Leukoc Biol.
29. Ito T, Allen R M, Carson W Ft, Schaller M, Cavassani K A et al. (2011) The critical role of Notch ligand Delta-like 1 in the pathogenesis of influenza A virus (H1N1) infection. PLoS Pathog 7(11): e1002341.
30. Jiang J, Hui C C (2008) Hedgehog signaling in development and cancer. Dev Cell 15(6): 801-812.
31. Klusza S, Deng W M (2011) At the crossroads of differentiation and proliferation: precise control of cell-cycle changes by multiple signaling pathways in *Drosophila* follicle cells. Bioessays 33(2): 124-134.
32. Kobasa D, Jones S M, Shinya K, Kash J C, Copps J et al. (2007) Aberrant innate immune response in lethal infection of macaques with the 1918 influenza virus. Nature 445 (7125): 319-323.
33. Kochs G, Garcia-Sastre A, Martinez-Sobrido L (2007) Multiple anti-interferon actions of the influenza A virus NS1 protein. J Virol 81(13): 7011-7021.
34. Kopan R, Ilagan M X (2009) The canonical Notch signaling pathway: unfolding the activation mechanism. Cell 137(2): 216-233.
35. Lamb R A, Krug, R. M (2001) Othromyxoviridae: the viruses and their replication. In: Knipe D M, Howley, P. M., editor. Fundamental Virology. Lippincott Williams & Wilkins, Philadelphia, Pa.
36. Lecuit T, Cohen S M (1998) Dpp receptor levels contribute to shaping the Dpp morphogen gradient in the *Drosophila* wing imaginal disc. Development 125(24): 4901-4907.
37. Marks S A, Kalderon D (2011) Regulation of mammalian Gli proteins by Costal 2 and PKA in *Drosophila* reveals Hedgehog pathway conservation. Development 138(12): 2533-2542.
38. Melen, K., Kinnunen, L., Fagerlund, R., Ikonen, N., Twu, K. Y., Krug, R. M., and Julkunen, I. (2007). Nuclear and nucleolar targeting of influenza A virus NS1 protein: striking differences between different virus subtypes. J Virol 81, 5995-6006.
39. Min, J. Y., Li, S., Sen, G. C., and Krug, R. M. (2007). A site on the influenza A virus NS1 protein mediates both inhibition of PKR activation and temporal regulation of viral RNA synthesis. Virology 363, 236-243.
40. Nellen D, Burke R, Struhl G, Basler K (1996) Direct and long-range action of a DPP morphogen gradient. Cell 85(3): 357-368.
41. Ohlmeyer, J. T., and Kalderon, D. (1998). Hedgehog stimulates maturation of Cubitus interruptus into a labile transcriptional activator. Nature 396, 749-753.
42. Pereira Tde A, Witek R P, Syn W K, Choi S S, Bradrick S et al. (2010) Viral factors induce Hedgehog pathway activation in humans with viral hepatitis, cirrhosis, and hepatocellular carcinoma. Lab Invest 90(12): 1690-1703.
43. Philips G M, Chan I S, Swiderska M, Schroder V T, Guy C et al. (2011) Hedgehog signaling antagonist promotes regression of both liver fibrosis and hepatocellular carcinoma in a murine model of primary liver cancer. PLoS One 6(9): e23943.
44. Panin V M, Irvine K D (1998) Modulators of Notch signaling. Semin Cell Dev Biol. 9(6): 609-17.
45. Pogach M S, Cao Y, Millien G, Ramirez M I, Williams M C (2007) Key developmental regulators change during hyperoxia-induced injury and recovery in adult mouse lung. J Cell Biochem 100(6): 1415-1429.
46. Quinlivan, M., D. Zamarin, A. Garcia-Sastre, A. Cullinane, T. Chambers, and P. Palese. 2005. Attenuation of equine influenza viruses through truncations of the NS1 protein. J Virol 79:8431-8439.

47. Reiter L T, Potocki L, Chien S, Gribskov M, Bier E (2001) A systematic analysis of human disease-associated gene sequences in *Drosophila melanogaster*. Genome Res 11(6): 1114-1125.
48. Selman M, Pardo A, Kaminski N (2008) Idiopathic pulmonary fibrosis: aberrant recapitulation of developmental programs? PLoS Med 5(3): e62.
49. Smelkinson M G, Zhou Q, Kalderon D (2007) Regulation of Ci-SCFSlimb binding, Ci proteolysis, and Hedgehog pathway activity by Ci phosphorylation. Dev Cell 13(4): 481-495.
50. Solorzano, A., R. J. Webby, K. M. Lager, B. H. Janke, A. Garcia-Sastre, and J. A. Richt. 2005. Mutations in the NS1 protein of swine influenza virus impair anti-interferon activity and confer attenuation in pigs. J Virol 79:7535-7543.
51. St Johnston R D, Hoffmann F M, Blackman R K, Segal D, Grimaila R et al. (1990) Molecular organization of the decapentaplegic gene in *Drosophila melanogaster*. Genes Dev 4(7): 1114-1127.
52. Steel, J., A. C. Lowen, L. Pena, M. Angel, A. Solorzano, R. Albrecht, D. R. Perez, A. Garcia-Sastre, and P. Palese. 2009. Live attenuated influenza viruses containing NS1 truncations as vaccine candidates against H5N1 highly pathogenic avian influenza. Journal of virology 83:1742-1753.
53. Stewart G A, Hoyne G F, Ahmad S A, Jarman E, Wallace W A et al. (2003) Expression of the developmental Sonic Hedgehog (Shh) signalling pathway is up-regulated in chronic lung fibrosis and the Shh receptor patched 1 is present in circulating T lymphocytes. J Pathol 199(4): 488-495.
54. Talon J, Horvath C M, Polley R, Basler C F, Muster T et al. (2000) Activation of interferon regulatory factor 3 is inhibited by the influenza A virus NS1 protein. J Virol 74(17): 7989-7996.
55. Talon, J., M. Salvatore, R. E. O'Neill, Y. Nakaya, H. Zheng, T. Muster, A. Garcia-Sastre, and P. Palese. 2000. Influenza A and B viruses expressing altered NS1 proteins: A vaccine approach. Proc Natl Acad Sci USA 97:4309-662 4314.
56. Teleman A A, Cohen S M (2000) Dpp gradient formation in the *Drosophila* wing imaginal disc. Cell 103(6): 971-980.
57. Twu K Y, Noah D L, Rao P, Kuo R L, Krug R M (2006) The CPSF30 binding site on the NS1A protein of influenza A virus is a potential antiviral target. J Virol 80(8): 3957-3965.
58. Vincent, A. L., W. Ma, K. M. Lager, B. H. Janke, R. J. Webby, A. Garcia-Sastre, and J. A. Richt. 2007. Efficacy of intranasal administration of a truncated NS1 modified live influenza virus vaccine in swine. Vaccine 25:7999-8009.
59. Wang L., D. L. Suarez, M Pantin-Jackwood, M Mibayashi, A Garcia-Sastre, Y M Saif, and C-W Lee. Characterization of Influenza Virus Variants with Different Sizes of the Non-structural (NS) Genes and Their Potential as a Live Influenza Vaccine in Poultry. Vaccine, 26:3580-3586. 2008.
60. Wilson C W, Chuang P T (2010) Mechanism and evolution of cytosolic Hedgehog signal transduction. Development 137(13): 2079-2094.
61. Yu, K., Srinivasan, S., Shimmi, O., Biehs, B., Rashka, K. E., Kimelman, D., O'Connor, M. B., and Bier, E. (2000). Processing of the *Drosophila* Sog protein creates a novel BMP inhibitory activity. Development 127, 2143-2154.
62. Zhou, Q., and Kalderon, D. (2011). Hedgehog activates fused through phosphorylation to elicit a full spectrum of pathway responses. Dev Cell 20, 802-814.

What is claimed is:

1. A method for treating influenza viral infection comprising administering to a subject in need an effective amount of a composition comprising a pharmaceutically acceptable carrier and a compound that modulates at least one host protein that interacts with NS1 viral protein, and is an antagonist of a Hedgehog (Hh) signaling pathway, wherein the compound is vismodegib.

2. The method of claim 1, wherein said composition is used in combination with one or more other therapeutic agents known for preventing or reducing severity of influenza viral infection, or associated syndromes thereof.

* * * * *

UNITED STATES PATENT AND TRADEMARK OFFICE

CERTIFICATE OF CORRECTION

PATENT NO. : 9,095,579 B2
APPLICATION NO. : 13/761922
DATED : August 4, 2015
INVENTOR(S) : Ethan Bier et al.

It is certified that error appears in the above-identified patent and that said Letters Patent is hereby corrected as shown below:

In the Specification

Column 1, Lines 14-17, please replace the paragraph under the STATEMENT REGARDING FEDERALLY SPONSORED RESEARCH from "This invention was made in part with Government support under Grant Nos. R01 AI070654, R01 AI11772, and 1F32 AI078672-01A1 awarded by the National Institutes of Health. The Government has certain rights in the invention." to --This invention was made with government support under AI011772, AI070654, and AI078672 awarded by the National Institutes of Health. The government has certain rights in the invention.--

Signed and Sealed this
Second Day of December, 2025

John A. Squires
*Director of the United States Patent and Trademark Office*